US010457746B2

(12) United States Patent
Colombo et al.

(10) Patent No.: US 10,457,746 B2
(45) Date of Patent: Oct. 29, 2019

(54) COMPOUNDS BINDING TO JMJD6 WITH ANTIFIBROTIC ACTIVITY

(71) Applicant: FONDAZIONE IRCCS "ISTITUTO NAZIONALE DEI TUMORI", Milan (IT)

(72) Inventors: Mario Paolo Colombo, Milan (IT); Silvia Miotti, Milan (IT); Elda Tagliabue, Milan (IT); Sabina Sangaletti, Milan (IT)

(73) Assignee: FONDAZIONE IRCCS "INSTITUTO NAZIONALE DEI TUMORI", Milan (IT)

( * ) Notice: Subject to any disclaimer, the term of this patent is extended or adjusted under 35 U.S.C. 154(b) by 0 days.

(21) Appl. No.: 15/553,642

(22) PCT Filed: Feb. 26, 2016

(86) PCT No.: PCT/EP2016/054177
§ 371 (c)(1),
(2) Date: Aug. 25, 2017

(87) PCT Pub. No.: WO2016/135338
PCT Pub. Date: Sep. 1, 2016

(65) Prior Publication Data
US 2018/0044433 A1 Feb. 15, 2018

(30) Foreign Application Priority Data

Feb. 27, 2015 (IT) .............................. MI2015A0297

(51) Int. Cl.
| | |
|---|---|
| *A61K 39/395* | (2006.01) |
| *C07K 16/00* | (2006.01) |
| *C07K 16/46* | (2006.01) |
| *C07K 16/40* | (2006.01) |
| *A61K 45/06* | (2006.01) |
| *C07K 16/30* | (2006.01) |
| *A61K 39/00* | (2006.01) |

(52) U.S. Cl.
CPC ........ *C07K 16/40* (2013.01); *A61K 39/39558* (2013.01); *A61K 45/06* (2013.01); *C07K 16/30* (2013.01); *C12Y 114/11004* (2013.01); *A61K 2039/505* (2013.01); *C07K 2317/14* (2013.01); *C07K 2317/34* (2013.01); *C07K 2317/56* (2013.01); *C07K 2317/76* (2013.01)

(58) Field of Classification Search
None
See application file for complete search history.

(56) References Cited

U.S. PATENT DOCUMENTS

2007/0281318 A1* 12/2007 Korth ................ C07K 16/2872
435/7.1
2009/0068740 A1* 3/2009 Mizuno ................ C12N 5/0068
435/401

FOREIGN PATENT DOCUMENTS

| WO | WO 01/0066785 A1 | 9/2001 |
|---|---|---|
| WO | WO 2009/141609 A1 | 11/2009 |
| WO | WO 2010/101528 A1 | 9/2010 |

OTHER PUBLICATIONS

Alexander Wolf. Jmjd6 catalyzes lysine 5-hydroxylation on U2AF-65 and is a potential regulator of the splicing process. Dissertation of the Faculty of Biology Ludwig-Maximilians-University Munich, Germany 2009. pp. 1-124. Translation of p. 6 and Fig. 2. (Year: 2009).*
Paduch et al. Generating conformation-specific synthetic antibodies to trap proteins in selected functional states. Methods. Mar. 15, 2013; 60(1): 3-14. (Year: 2013).*
Anonymous: Collagen I Rat Tail 100 mg (35436):—ToxBank Gold Compounds and Biological Materials Wiki, Mar. 27, 2013, XP055269597, retrieved from the Internet: URL: http://wiki-toxbank.net/wiki/Collagen_1_rat_tail_100_mg_(354236) [retrieved on Apr. 29, 2016].
Arendt et al., "Stroma in Breast Development and Disease", *Semin Cell Dev Biol*. 2010; 21(1): 11-18.
Aslakson et al., "Selective Events in the Metastatic Process Defined by Analysis of the Sequential Dissemination of Subpopulations of a Mouse Mammary Tumor", *Cancer Res* 1992; 52: 1399-1405.
Böse et al., "The Phosphatidylserine Receptor Has Essential Functions During Embryogenesis but Not in Apoptotic Cell Removal", *J Biol* 2004; 3:15 (18 pages).
Brüggemann et al., "Human Antibody Production in Transgenic Animals", *Arch Immunol Ther Exp* 2015, 63:101-108.
Chang et al., "JMJD6 is a Histone Arginine Demethylase", *Science* 2007; 318: 444-447.
Cikala et al., "The Phosphatidylserine Receptor from Hydra is a Nuclear Protein with Potential Fe(II) Dependent Oxygenase Activity", *BMC Cell Biol* 2004; 5:26 (10 pages).
Cui et al., "Nuclear Localization of the Phosphatidylserine Receptor Protein via Multiple Nuclear Localization Signals", *Experimental Cell Research* 2004; 293:154-163.
Egeblad et al., "Dynamic Interplay Between the Collagen Scaffold and Tumor Evolution", *Curr Opin Cell Biol* 2010, 22(5): 697-706.
Fadok et al., "A Receptor for Phosphatidylserine-Specific Clearance of Apoptotic Cells", *Nature* 2000; 405: 85-90.
Giatromanolaki et al., "The Pathology of Tumor Stromatogenesis", *Cancer Biology & Therapy* 2000; 6(5): 639-645.
Hahn et al., "Genomic Structure and Expression of Jmjd6 and Evolutionary Analysis in the Context of Related JmjC Domain Containing Proteins", *BMC Genomics* 2008; 9:293 (26 pages).
Hahn et al., "Analysis of Jmjd6 Cellular Localization and Testing for its Involvement in Histone Demethylation", *PLoS One* 2010; 5(10): e13769 (13 pages).

(Continued)

Primary Examiner — Maher M Haddad
(74) Attorney, Agent, or Firm — Mueting, Raasch & Gebhardt, P.A.

(57) ABSTRACT

The present invention relates to the interaction between JMJD6 protein and collagen and to the possibility of inhibiting this interaction for the prevention and treatment of fibrosis and of tumor metastases. The invention further relates to a compound that is able to block the interaction between collagen and JMJD6 protein, in particular the invention relates to a new monoclonal antibody that recognizes JMJD6 and is able to block this interaction.

11 Claims, 20 Drawing Sheets
Specification includes a Sequence Listing.

(56) References Cited

OTHER PUBLICATIONS

Heim et al., "Jumonji Domain Containing Protein 6 (Jmid6) Modulates Splicing and Specifically Interacts with Arginine-Serine-Rich (RS) Domains of SR- and SR-like Proteins", *Nucleic Acids Res* 2014, 42(12): 7833-7850.
Köninger et al., "Phosphatidylserine Receptor in Chronic Pancreatitis: Evidence for a Macrophage Independent Role", *Annals of Surgery* 2005; 241(1): 144-151.
Kozlowski et al., "Metastatic Behavior of Human Tumor Cell Lines Grown in the Nude Mouse", *Cancer Res* 1984; 44:3522-3529.
Li et al., "Targeting the Cancer-Stroma Interaction: A Potential Approach for Pancreatic Cancer Treatment", *Curr Pharm Des.* 2012; 18(17): 2404-2415.
Lu et al., "The Extracellular Matrix: A Dynamic Niche in Cancer Progression", *J. Cell Biol.* 2012; 196(4): 395-406.
Martinez-Outschoorn et al., "Stromal-Epithelial Metabolic Coupling in Cancer: Integrating Autophagy and Metabolism in the Tumor Microenviroment", *Int J Biochem Cell Biol.* 2011; 43(7): 1045-1051.
Moore et al., "In Vitro Maintenance of Highly Purified, Transplantable Hematopoietic Stem Cells", *Blood* 1997; 89(12): 4334-4347.
Poulard et al., "JMJD6 Regulates ERα Methylation on Arginine", *PLoS One* 2014; 9(2): e87982 (9 pages).
Qi et al., "TNFSF15 Inhibits Vasculogenesis by Regulating Relative Levels of Membrane-Bound and Soluble Isoforms of VEGF Receptor 1", *Proceedings of the National Academy of Sciences*, 2013, 10(34): 13863-13868.
Rose et al., "Inhibition of 2-Oxoglutarate Dependent Oxgenases", *Chem Soc Rev* 2011 40(8): 4364-4397.
Sangaletti et al., "Macrophage-Derived SPARC Bridges Tumor Cell-Extracellular Matrix Interactions toward Metastasis", *Cancer Res* 2008; 68(21): 9050-9059.
Sangaletti et al., "SPARC Oppositely Regulates Inflammation and Fibrosis in Bleomycin Induced Lung Damage", *Am J Pathol* 2011, 179(6): 3000-3010.
Sherman et al., "Minireview: Nuclear Receptors as Modulators of the Tumor Microenvironment", *Cancer Prev Res (Phila).* 2012; 5(1): 3-10.
Teyssier et al., "Drug-Related Chromosomal Changes in Chemo Resistant Human Ovarian Carcinoma Cells", *Cancer Genet Cytogenet* 1989, 39(1): 35-43.
Tibrewal et al., "Characterization of the Biochemical and Biophysical Properties of the Phosphatidylserine Receptor (PS-R) Gene Product", *Mol Cell Biochem* 2007; 304: 119-125.
Tripodo et al., "Stromal SPARC Contributes to Fibrotic Detrimental Changes Associated with Myeloproliferation whereas its Deficiency Favors Myeloid Cell Expansion", *Blood* 2012; 120(17): 3541-3554.
Unoki et al., "Lysyl 5-Hydroxylation, a Novel Histone Modification, by Jumonji Domain Containing 6 (JMJD6)", *J Biol Chem.* 2013; 288(9):6053-62.
Vandivier et al., "Elastase-Mediated Phosphatidylserine Receptor Cleavage Impairs Apoptotic Cell Clearance in Cystic Fibrosis and Bronchiectasis", *J Clin Invest* 2002; 109(5): 661-670.
Wang et al., "JMJD6 Promotes Colon Carcinogenesis Through Negative Regulation of p53 by Hydroxylation", *PLoS Biol.* 2014; 12(3): e1001819 (18 pages).
Webby et al., "Jmjd6 Catalyses Lysyl-Hydroxylation of U2AF65, a Protein Associated with RNA Splicing", *Science* 2009; 325: 90-93.
Wynn et al., "Mechanisms of Fibrosis: Therapeutic Translation for Fibrotic Disease", *Nat Med* 2012; 18(7): 1028-1040.
Yang et al., "A Lysine-Rich Motif in the Phosphatidylserine Receptor PSR-1 Mediates Recognition and Removal of Apoptotic Cells", *Nat Commun* 2015; 6: 5717 (12 pages).
Zakharova et al., "Endogenous Jmjd6 Gene Product is Expressed at the Cell Surface and Regulates Phagocytosis in Immature Monocyte-Like Activated THP-1 Cells", *J Cell Physiol* 2009; 221: 84-91.
PCT International Search Report (PCT/ISA/210) and Written Opinion (PCT/ISA/237) for PCT/EP2016/054177, dated May 2, 2016 (11 pages).

\* cited by examiner

FIG. 7'

```
  1 MNHKSKKRIR  EAKRSARPEL  KDSLDWTRHN  YYESFSLSPA  AVADNVERAD
 51 ALQLSVEEFV  ERYERPYKPV  VLLNAQEGWS  AQEKVTLERL  KRKYRNQKFK
101 CGEDNDGYSV  KMKMKYYIEY  MESTRDDSPL  YIFDSSYGEH  PKRRKLLEDY
151 KVPKFFTDDL  FQYAGEKRRP  PYRWFVMGPP  RSGTGIHIDP  LGTSAWNALV
201 QGHKRWCLFP  TSTPRELIKV  TRDEGGNQQD  EAITWFNVIY  PRTQLPTWAP
251 EFKPLEILQK  PGETVFVPGG  WWHVVLNLDT  TIAITQNFAS  STNFPVVWHK
301 TVRGRPKLSR  KWYRILKQEH  PELAVLADSV  DLQESTGIAS  DSSSDSSSS
351 SSSSSDSDSE  CESGSEGDGT  VHRRKKRRTC  SMVGNGDTTS  QDDCVSKERS
401 SSR
```

COMPOUNDS BINDING TO JMJD6 WITH ANTIFIBROTIC ACTIVITY

CONTINUING APPLICATION DATA

This application is a U.S. National Stage Application of International Application No. PCT/EP2016/054177, filed Feb. 26, 2016, which was published in English on Sep. 1, 2016, as International Publication No. WO 2016/135338 A1. International Application No. PCT/EP2016/054177 claims priority to Italian Application No. MI2015A000297 filed Feb. 27, 2015.

SEQUENCE LISTING

This application contains a Sequence Listing electronically submitted via EFS-Web to the United States Patent and Trademark Office as an ASCII text file entitled "0555-000001US01_ST25.txt" having a size of 16 kilobytes and created on May 14, 2019. The information contained in the Sequence Listing is incorporated by reference herein.

FIELD OF THE INVENTION

The present invention relates to the interaction between JMJD6 protein and collagen and to the possibility of inhibiting this interaction for the prevention and treatment of fibrosis and of tumor metastases. The invention further relates to a compound that is able to block the interaction between collagen and JMJD6 protein, in particular the invention relates to a new monoclonal antibody that recognizes JMJD6 and is able to block this interaction.

BACKGROUND ART

Fibrosis is the final pathologic result common to several chronic inflammatory diseases. Although collagen deposition is an unavoidable and generally reversible step of wound healing, normal tissue repair can evolve into an irreversible and progressive fibrotic response if tissue damage is serious or repeated or if healing response gets out of control. Fibrosis is defined as an excessive accumulation of fibrous connective tissue, i.e. of components of the extracellular matrix (ECM) such as collagen and fibronectin around the inflammatory or damaged tissue, which can lead to permanent scars, organ dysfunction and eventually to death, as has been seen in the late stage of hepatic and renal disease, in idiopathic pulmonary fibrosis (IPF) and in heart failure. Fibrosis is also a pathologic feature of several chronic autoimmune diseases including dermatosclerosis, rheumatoid arthritis, Crohn's disease, ulcerative colitis, myelofibrosis and systemic lupus erythematosus. Moreover, fibrosis affects tumor invasion and metastases, chronic rejection and the pathogenesis of several progressive myopathies (Wynn et al., Nat. Med 2012; 18(7): 1028-1040).

Despite the fact that fibrogenesis is recognized as one of the main causes of morbidity and mortality in most chronic inflammatory and autoimmune diseases, few treatments are available specifically addressing fibrosis pathogenesis.

Fibrotic phenomena and/or alterations of the extracellular matrix also play an important role in tumor diseases. The local microenvironment, or niche, of a tumor cell is indeed a key to cancer development. An important component of this niche is the extracellular matrix (ECM), a complex network of macromolecules comprising collagen and fibronectin and having peculiar physical, biochemical and biomechanical properties. Though being closely controlled during embryonic development and organ homeostasis, EMC is remodeled in diseases like cancer. An abnormal ECM affects transformation promoting cancer progression and metastasis. As a matter of fact, ECM abnormalities affect the behavior of stromal, endothelial and immune system cells creating an inflammatory and pro-tumorigenic environment (Pengfei et al., J. Cell Biol. 2012; 196(4): 395-406; Arendt et al., Semin Cell Dev Biol. 2010; 21(1): 11-18; Martinez-Outschoorn et al., Int J Biochem Cell Biol. 2011; 43(7): 1045-1051; Li et al., Curr Pharm Des. 2012; 18(17): 2404-2415; Sherman et al., Cancer Prev Res (Phila). 2012; 5(1): 3-1; Giatromanolaki et al., Cancer Biology & Therapy 2000; 6(5): 639-645). Therefore, new therapeutic agents should aim at preventing both the progressive ECM deregulation and the activation of stromal cells by acting upon the local tumor microenvironment.

Finally, it is known that the presence of a strong fibrotic component, produced by microenvironment cells and by tumor cells themselves subjected to epithelial mesenchymal transition, can affect the response to chemotherapeutic therapy. As a matter of fact, the content and structural organization of collagens, by increasing the density of the matrix and the pressure of the interstitial fluid, can negatively affect the accessibility of drugs to tumor (Egebla et al., Curr Opin Cell Biol 2010. 22: 697-706). Therefore, the administration in combination with an antifibrotic agent can be useful in enhancing the activity of chemotherapeutic drugs, enabling to administer to the patient a smaller drug dose and as a result to reduce the adverse effects thereof, or anyhow to obtain a higher therapeutic effectiveness. The occurrence of fibrotic phenomena is also an adverse effect of radiotherapy and of some chemotherapeutic drugs, such as e.g. bleomycin, fludarabine and methotrexate. Therefore, the combined administration of radiotherapy or of these chemotherapeutic drugs with antifibrotic agents can inhibit fibrosis-related tissue damage and thus reduce the adverse effects associated to the administration thereof.

The gene for JMJD6 was cloned in 2000 and at first the protein was incorrectly classified as a transmembrane protein. Based on the characteristics of the residues present on the putative extracellular domain of the protein and on in-vitro data, it was assumed at first that this protein was located on the surface of macrophages, where it was able to bind phosphatidylserine, thus regulating the phagocytosis of apoptotic cells induced by the exposition of this specific phospholipid on the surface thereof. Based on these experimental evidence, the protein was classified at first as a phosphatidylserine receptor (Fadok et al., Nature 2000; 405: 85-90).

However, these initial assumptions were discredited by following studies, which conversely pointed out that JMJD6 is not a transmembrane protein but it is only located in the nucleus (Cikala et al., BMC Cell Biol 2004; 5:26; Cui et al., Experimental Cell Research 2004; 293:154-163.

Moreover, also its role in the removal of apoptotic cells was confuted (Bose et al., J Biol 2004; 3:15). In Zakharova et al., (J Cell Physiol 2009; 221: 84-91) it is stated that JMJD6 is expressed on the surface of immature phagocytes, but it is translocated into the nucleus as a result of cell differentiation.

The protein was recognized at the same time as a member of the family of proteins containing the JmjC domain and renamed JMJD6 by the International Committee for Standardized Genetic Nomenclature in Mice (ICSGNM).

In affinity with other members of this family, JMJD6 was attributed a demethylation activity on arginine residues of histone 3 and 4 (Chang et al., Science 2007; 318: 444-447).

However, the presence of this enzymatic activity is currently under discussion since the observation could not be reproduced in following studies (Hahn et al., PLos One 2010; 5(10): 13769 and Webby et al., Science 2009; 325: 90-93). Webby et al. assumes that this inconsistency can be due to the fact that the ability to catalyze demethylation of arginine residues is very weak and therefore not always detectable.

More recently, it was proved that the main enzymatic activity JMJD6 is on the contrary the hydroxylation of lysine residues. Through this activity on some splicing factors, the protein plays an important role in the regulation of alternative splicing and thus in gene regulation (Webby et al., Science 2009; 325: 90-93; Hahn et al., BMC Genomics 2008; 9:293 and Hahn et al., pLos One 2010; 5(10): e13769); Unoki M et al., J Biol Chem. 2013; 288(9):6053-62. Poulard C et al., PLoS One 2014; 9(2):e87982; Wang F et al., PLoS Biol. 2014; 12(3):e1001819; Heim A et al., Nucleic Acids Res. 2014; 42 (12): 7833-50.

More recent literature agrees on considering JMJD6 as a nuclear protein with functions related to the regulation of gene expression.

Koninger et al., Annals of Surgery 2005; 241 (1): 144-151; Vandivier et al., Journal Clinic Invest 2002; 109(5): 661-670, and WO01/0066785 assume that the stimulation of phosphatidylserine receptor (first name of JMJD6) can induce the secretion of TGF-beta, a molecule whose profibrotic activity is known. However, this assumption arises from experimental observations which attributed a role to the phosphatidylserine receptor (PSR-1) in the phagocytosis of apoptotic cells, which role was then rejected. However, although recent literature no longer attributes this function to JMJD6, PSR-1 has been recently reported to recognize phosphatidylserine on the surface of apoptotic cells, in *C. Elegans* (Yang H. et al. Nat Commun 2015; 6: 5717).

WO2009141609 describes modulators of JMJD6 enzymatic activity for the treatment of diseases related to an abnormal RNA splicing, such as e.g. tumor diseases. WO2010101528 describes JMJD6 as a diagnostic and prognostic bio-marker of breast cancer, which can distinguish between the tumor at an initial stage and a metastatic and/or advanced tumor. In this context, the document assumes the use of JMJD6 antagonists, including antibodies, in the prevention and reduction of tumor metastases. Neither does the document provide details about the antibody characteristics required to obtain a desired antagonist activity, nor a role of JMJD6 outside the cell, in the stroma, is assumed, nor a direct involvement thereof in fibrosis is assumed. Lastly, Wang F et al., PLoS Biol. 2014; 12(3):e1001819 describes that depletion of JMJD6 by two specific siRNA represses p53-dependent colon cell proliferation and tumorigenesis, a finding that neither makes reference to the protein outside the cells and its interaction with collagen on other ECM proteins nor to fibrosis.

SUMMARY OF THE INVENTION

The present inventors, contrary to what is described in the literature, have now found that JMJD6 protein is not located only in the nucleus, but it is also secreted in the extracellular environment where it plays a role in the formation and/or organization of the extracellular matrix. In particular, they have found that this is mediated by means of JMJD6 protein binding to collagen.

The present inventors have further found that the block of the interaction between collagen and JMJD6 protein is useful in the prevention and/or treatment of fibrosis, including the cancer associated fibrosis, and in the prevention and treatment of tumor metastasis.

Moreover, the inventors have generated a new monoclonal antibody, named P4E11 or P4, which is able to recognize a specific conformational epitope of JMJD6 protein. This antibody can interfere with JMJD6 protein binding to collagen and through this action inhibits fibrotic phenomena in normal or tumor tissues and the development of metastases. The antibody is therefore useful in the prevention and/or treatment of fibrosis and of tumor metastases. Moreover, if administered in association with radiotherapy or with known chemotherapeutic drugs, it facilitates the access of chemotherapeutic drugs to the tumor, enhancing their activity and effectiveness, reducing their therapeutically effective dose and, as a result, lowering their toxicity. The present inventors have also identified the aminoacid sites on the JMD6 protein that are blocked by the antibody and are responsible for the binding of JMJD6 with collagen. Compounds that bind to these sequences block the interaction between collagen and JMJD6 protein.

Therefore, a first object of the present invention relates to a compound that is able to block the interaction between collagen and JMJD6 protein wherein said compound binds to one or more portions of at least 5 consecutive amino acids of at least 2 of the following amino acid sequences of JMJD6 protein:

```
                                        (SEQ ID 33)
    RIREAKR, (SEQ ID 34)
    RKYRNQK, (SEQ ID 35)
    KMKYYIE, (SEQ ID 36)
    PKRRKLL, (SEQ ID 37)
    RPPYRWF, (SEQ ID 38)
    KRWCLFP,

SEQ ID 39)
    VPGGWWHVVLNLDTTIAITQN, (SEQ ID 40)
    VRGRPKLSR KWYRI, (SEQ ID 41)
    HRRKKRR.
```

A second object of the present invention relates to a monoclonal antibody, or a fragment thereof, against JMJD6 protein, characterized in that this antibody binds only to said protein in its native conformation and not in its heat-denaturated conformation or to linear peptides of the protein itself and/or this antibody recognizes a heat-sensitive conformational epitope, preferably it recognizes the epitope consisting of an amino acid sequence comprising one or more portions of at least 5 amino acids of at least 2 of the following amino acid sequences of said protein:

RIREAKR, (SEQ ID 33)

RKYRNQK, (SEQ ID 34)

KMKYYIE, (SEQ ID 35)

PKRRKLL, (SEQ ID 36)

RPPYRWF, (SEQ ID 37)

KRWCLFP, (SEQ ID 38)

VPGGWWHVVLNLDTTIAITQN, (SEQ ID 39)

VRGRPKLSR KWYRI, (SEQ ID 40)

HRRKKRR. (SEQ ID 41)

A third object of the present invention relates to the above compound or antibody for use as a medicament.

A fourth object of the present invention relates to the above compound or antibody for use in the prevention and/or treatment of fibrosis.

A fifth object of the present invention relates to the above compound or antibody for use in the prevention and/or treatment of tumor metastases.

A sixth object of the present invention relates to the above compound or antibody for use in association with radiotherapy and/or chemotherapy in the treatment of a tumor.

A seventh object of the present invention relates to a pharmaceutical composition comprising the above compound or antibody, and at least one pharmaceutically acceptable carrier and/or excipient.

An eighth object of the present invention relates to combination of the above compound or antibody with at least one chemotherapeutic drug.

A ninth object of the present invention relates to the above combination for use in the treatment of a tumor.

A tenth object of the present invention relates to a hybridoma for the production of the above compound wherein the compound is a monoclonal antibody, preferably a hybridoma deposited with the Autorità Internazionale di Deposito (AID) Centro di Biotecnologie Avanzate (CBA)—Interlab Cell Line Collection (ICLC) of Genoa (Italy), access no. PD 15001, deposited on Jan. 13, 2015, and available from IRCCS Azienda Ospedaliera Universitaria San Martino-IST Istituto Nazionale per la Ricerca sul Cancro, L. go R. Benzi, 10, 16132 GENOVA, ITALY.

An eleventh object of the present invention relates to the antibody obtained from the hybridoma as defined above.

A twelfth object of the present invention relates to a method for the prevention and/or treatment of a disease selected from fibrosis and tumor metastases in a patient by administering a compound or an antibody as defined above in a pharmaceutically effective amount in order to prevent and/or treat this disease.

A thirteenth object of the present invention relates to a method for treating tumors in a patient by administering a compound or an antibody as defined above in a pharmaceutically effective amount in association with radiotherapy and/or chemotherapy.

Definitions

According to the present invention, JMJD6 is defined as a protein having the amino acid sequence contained in UniProt database under access number Q6NYC1, or variants or truncated forms thereof having a sequence with an homology of at least 85%, preferably of at least 90%, more preferably of at least 95%, still more preferably of at least 98% with the aforesaid sequence.

As used here, the wording "pharmaceutically effective amount" of a compound according to the present invention shall be an amount of active agent that is able to prevent or at least slow down (reduce) fibrosis and/or metastases and to reduce the dosage of any known chemotherapeutic drugs administered in combination, thus reducing the adverse effects of the latter. Dosages and administration of the active agent in a pharmaceutical composition can be determined by a person with ordinary skills in the technique of clinical pharmacology or pharmacokinetics, see e.g. Mordenti and Rescigno, 1992 Pharmaceutical Research, 9:17-25; Mordenti et al., 1991 Pharmaceutical Research, 8:1351-1359; and Mordenti and Chappell, The use of interspecies scaling in toxicokinetics and New Drug development, Yacobi et al., (Eds) Pergamon Press: NY, 1989, pages 42-96. An effective amount of the active agent to be used therapeutically shall depend for instance on the therapeutic objectives, the administration route and the mammal's condition. As a result, it shall be necessary for the physician to adjust dosage and change the administration route as required in order to obtain the optimal therapeutic effect. A typical daily dose can vary from about 10 ng/kg to 100 mg/kg of body weight of the mammal or more per day, preferably from about 1 µg/kg/day to 10 mg/kg/day.

DESCRIPTION OF THE FIGURES

As shown in FIG. 4, frame B, the band of about 52 kDa, quantitatively less represented, can only be seen in 150 and 50 ng immunoprecipitates of JMv1 rec.

Frame B shows an immunofluorescence on adhering cells: MeWo cells transfected with JM 5'/FLAG, after two days from transfection. The FLAG DDK epitope is expressed on the transfected cells only and these are positive also with anti-JMJD6 s.c., while there is no reactivity with P4E11.

Figure 7:
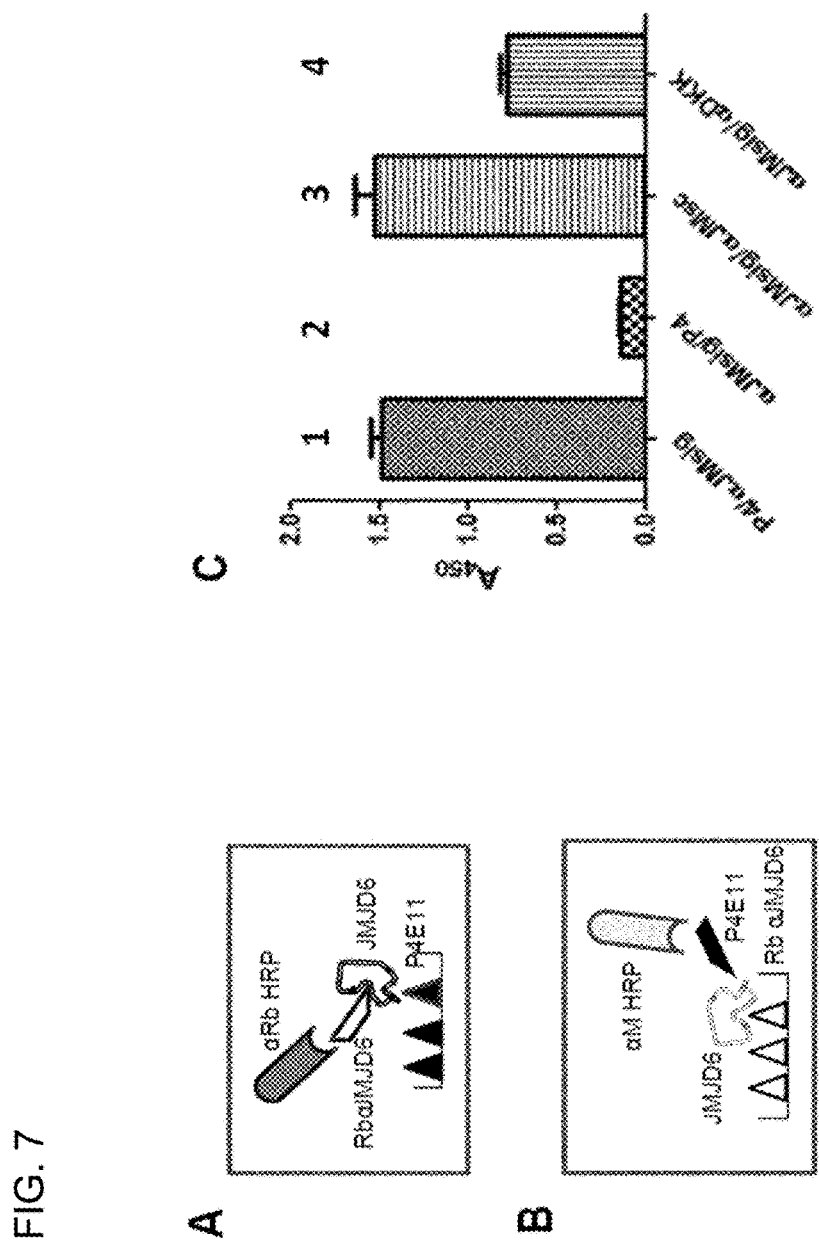

FIG. 7 shows an ELISA test in which P4E11 antibody is used for capturing JMJD6 rec protein, which is then detected by the polyclonal anti-JMJD6 antibody Sigma (example A), or in which P4E11 is used as antibody for detecting the recombinant protein captured by the polyclonal antibody Sigma adhering to the plate (example B). Frame C shows the results obtained using JMJD6v1 rec, which indicate that, only if the test is performed as shown in A (column 1), but not as in B (column 2), recombinant JMJD6 protein can be detected by this antibody combination. Columns 3 and 4 show that JMJD6rec is detected if instead of P4E11, the monoclonal anti-JMJD6 antibody Santa Cruz (s.c.) or anti-FLAG DDK antibody are used.

FIG. 7' reports the amino acidic sequence of JMJD6. Sequences involved in the binding of P4E11 have been identified by sequencing the peptides derived from proteolytic treatment of JMJD6v2rec in the presence of P4E11 or of an unrelated mAb (see detailed description in Materials and Methods). From differential analysis resulted that 6 sequences (in bold) participate to the formation of the epitope recognized by P4E11. Three of them are located at the N-term of JMJD6 protein, and three inside the JmjC domain (marked by the black bold line). The sequences bound both by P4E11 and by the unrelated mAb (in italic) have been considered non-specific. The coll1 binding sites overlapping to P4E11 binding sequences are three and are underlined with the dashed line. Sequence #1 (RSARPEL) is included in SEQ ID 10 (RIREAKRSARPELK-peptide 2), sequence #2 (MKYYIEYMESTR-peptides 16-17) includes SEQ ID 35 (MKYYIE), and sequence #3 (SGTGIHIDPL-GTSAWNALVQGHKRWCLFPTSTPRE-peptides 26-30) includes SEQ ID 38 (KRWCLFP).

Figure 8:
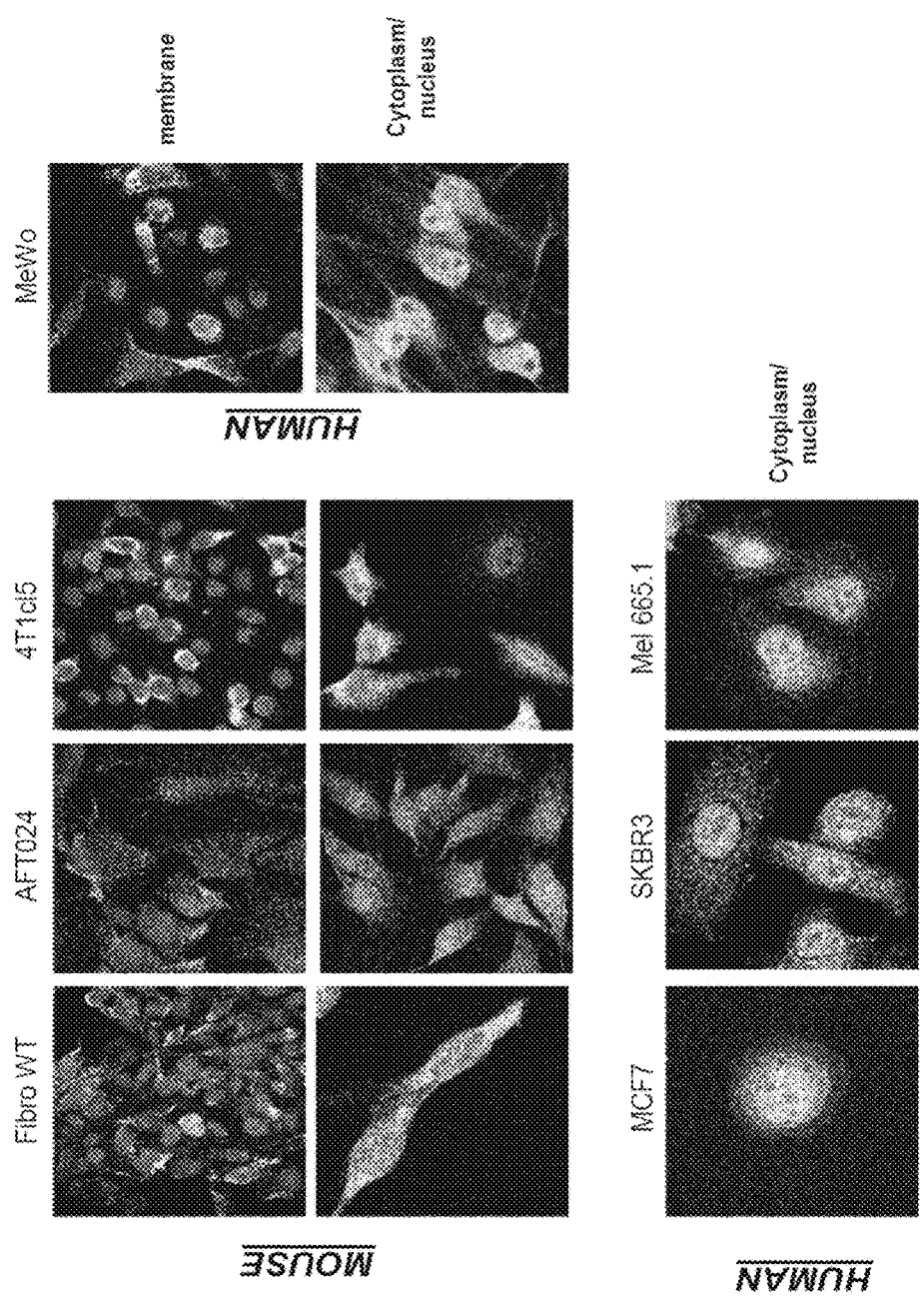

FIG. 8 shows the result of an immunofluorescence analysis with a confocal microscope with the P4E11 antibody assayed on adhering cells. The cells were fixed with 2% paraformaldehyde (PFA) for a membrane localization or fixed with PFA and permeabilized with 0.1% Triton-X100 for an intracellular localization (cytoplasm/nucleus) of the target protein. The marking is shown both in the membrane and in intracellular position of immortalized fibroblasts (FibroWT), of the stromal cell line AFT024, of the mammary cancer line 4T1cl5 and of the human melanoma line MeWo; the intracellular marking of human lines of mammary cancer, MCF7 and SKBR3, of melanoma Mel665.1 is also shown.

Figure 9:
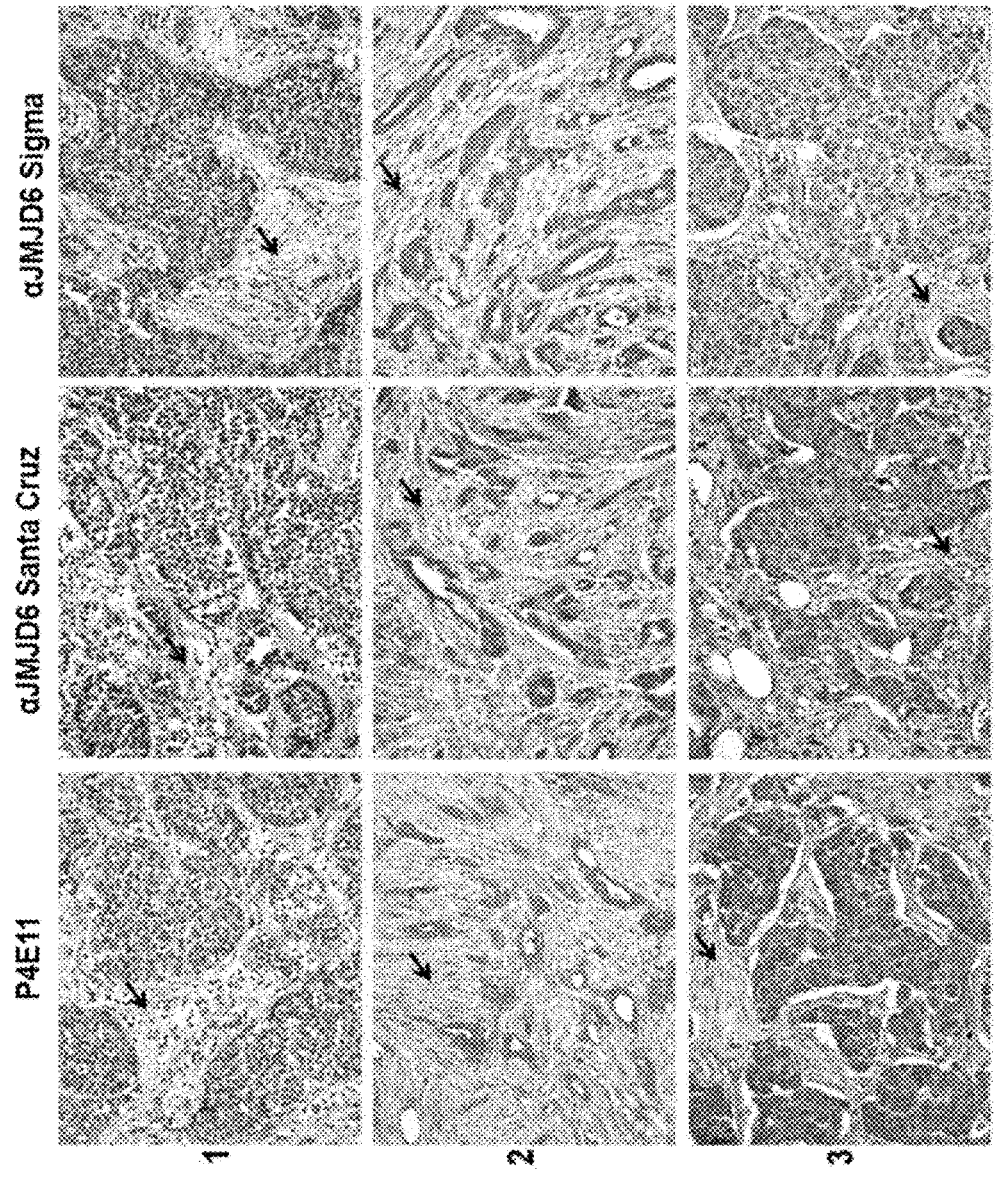

FIG. 9 shows the immunohistochemical analysis of three exemplary cases from a panel of 22 cases of human mammary cancer, stained with P4E11 antibody in parallel to the two commercial anti-JMJD6 antibodies (polyclonal antibody Sigma, monoclonal antibody Santa Cruz). In all the cases the marking has a heterogeneous distribution (cytoplasm, nucleus, extracellular) with each one of the antibodies used. The arrows show the marking of the stroma.

Figure 10:
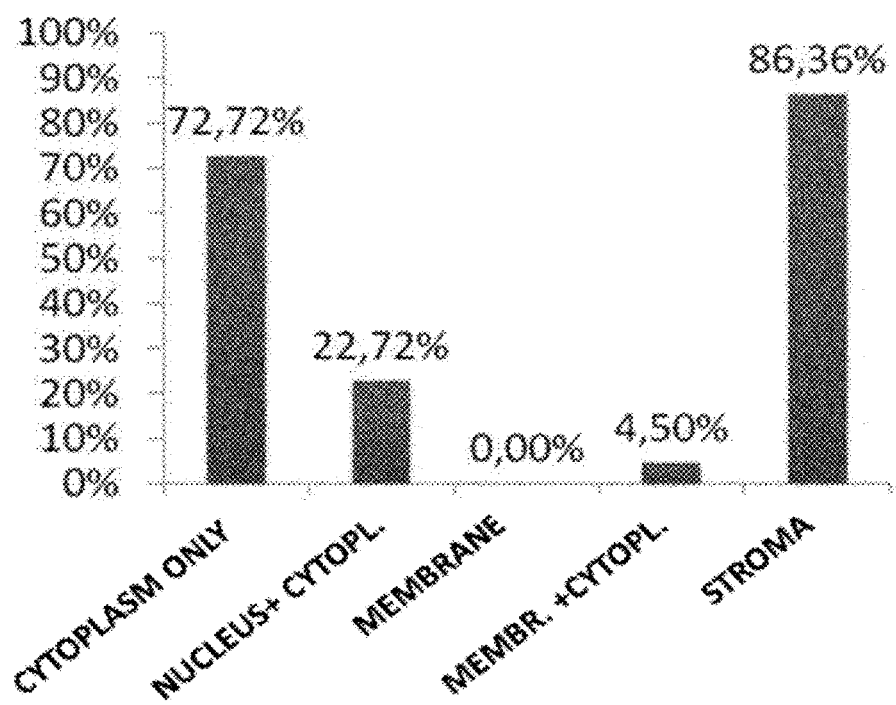

FIG. 10 shows the result of the immunohistochemical analysis performed on 22 cases of human mammary cancer, stained with P4E11 antibody. The ordinates represent the percentage of positive cases, whereas the abscissae show the various cellular and extracellular compartments in which the signal was detected.

Figure 11:
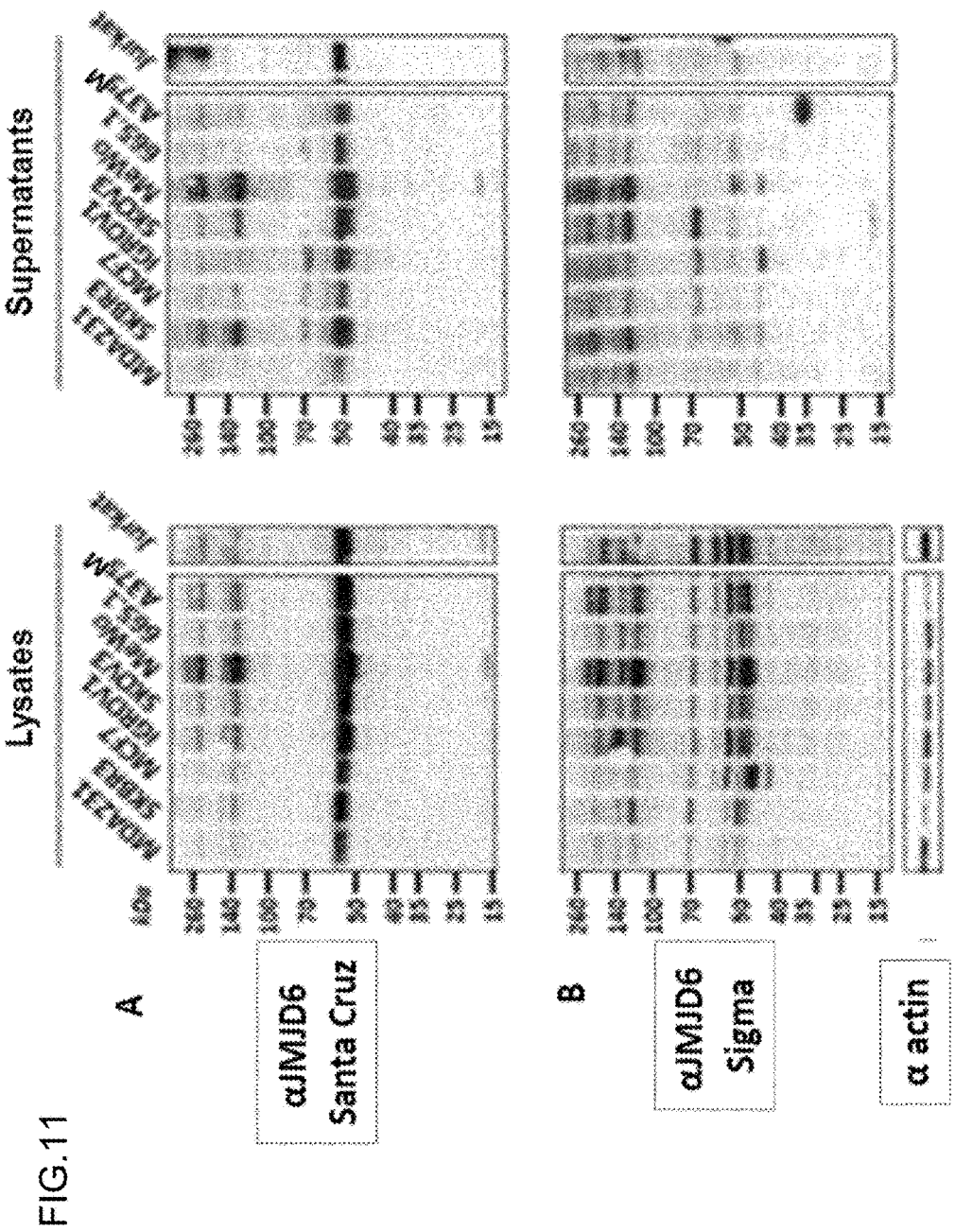

FIG. 11, frame A and B, shows a Western Blot of cell lysates of human tumor lines and of the respective culture supernatants, in which JMJD6 is detected with the antibody Sigma or Santa Cruz, respectively, as described in Example 2.

Figure 12:
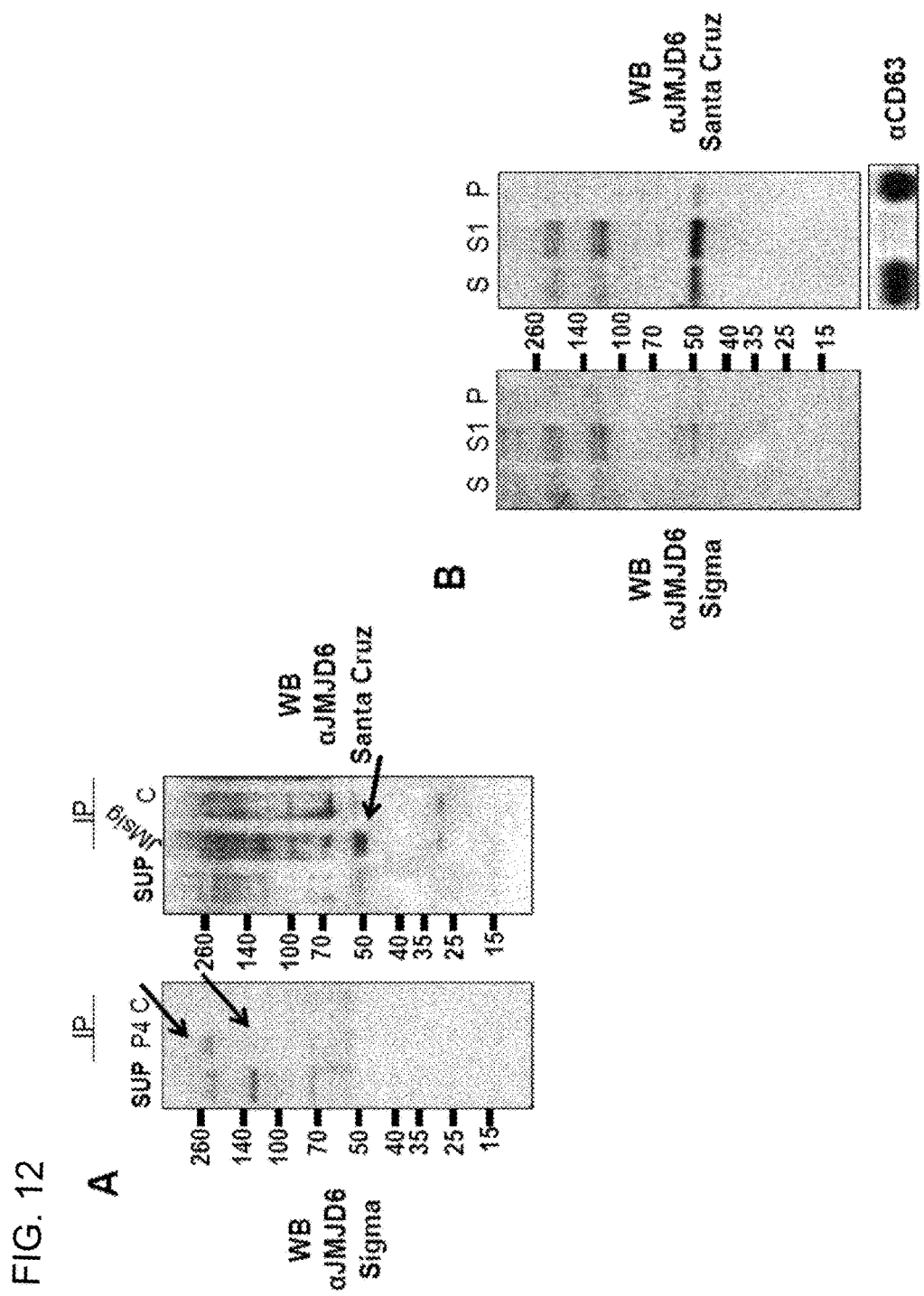

FIG. 12 shows in frame A a WB of the supernatant of MeWo cells (SUP) and of the product immunoprecipitated by incubation of this supernatant with P4E11 (P4) or with anti-JMJD6 antibody by Sigma (JMsig). Immunoprecipitate C represents the control obtained with unrelated antibodies. The detection was performed with anti-JMJD6 antibody by Sigma or by Santa Cruz, respectively.

FIG. 12 shows in panel B a WB of supernatant of MeWo cells (S) and of the supernatant (S1) and of the pellet (P) obtained after ultracentrifugation of S (100.000×g 2 h), followed by detection with anti-JMJD6 antibodies by Sigma and Santa Cruz. The same samples were assayed with an anti-CD63 antibody, a marker of exosomes precipitating in the pellet.

Figure 13:
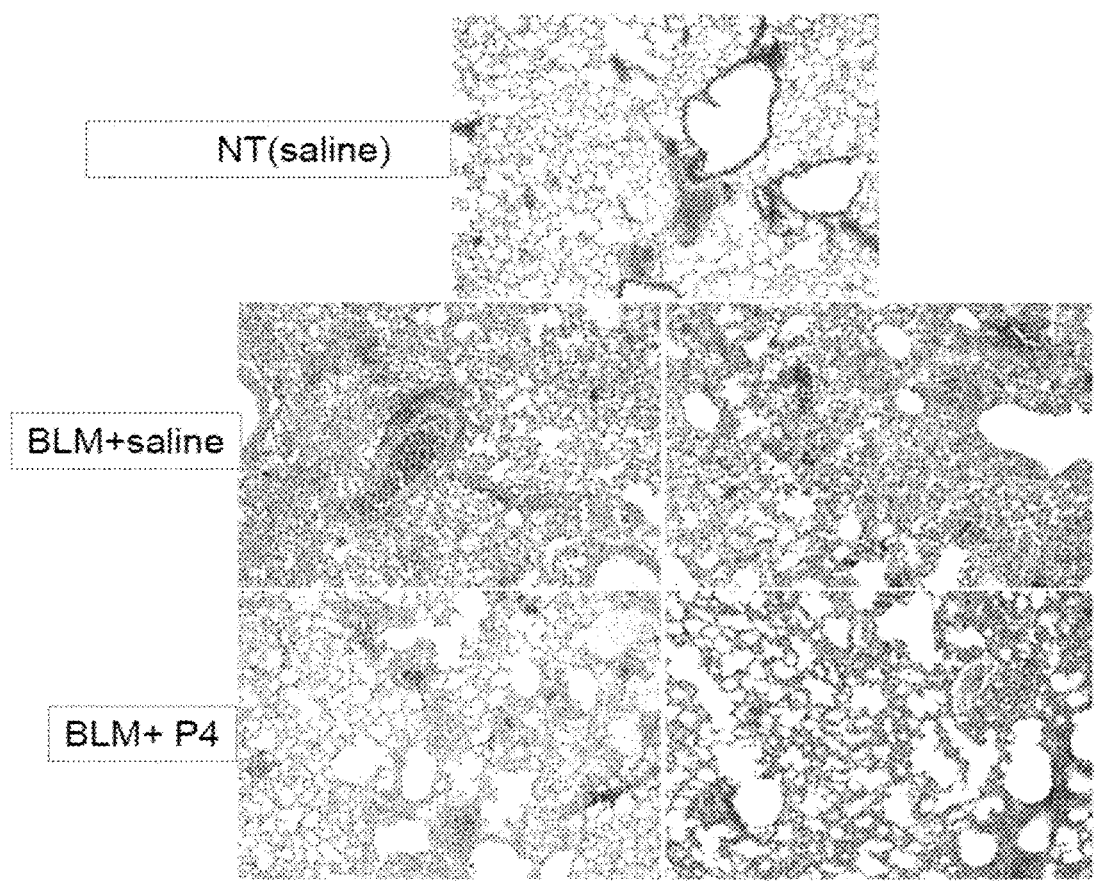

FIG. 13 shows histological sections of mouse lung stained with Hemat/Eos, untreated (saline) or treated with bleomycin (BLM+ saline) or with bleomycin and P4E11 antibody (BLM+P4).

Figure 14:
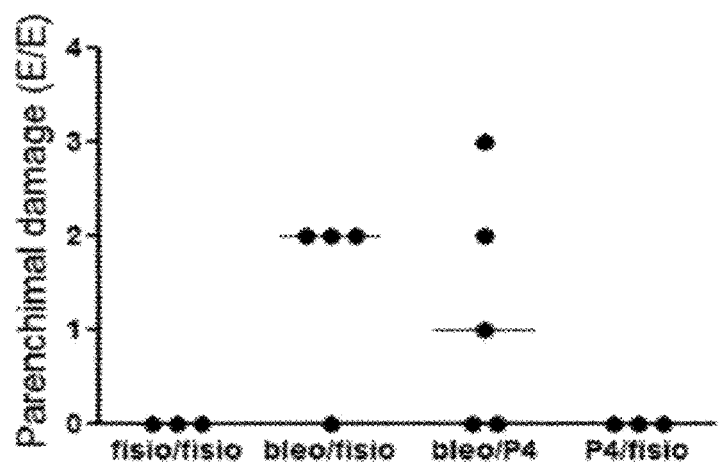
Figure 14:
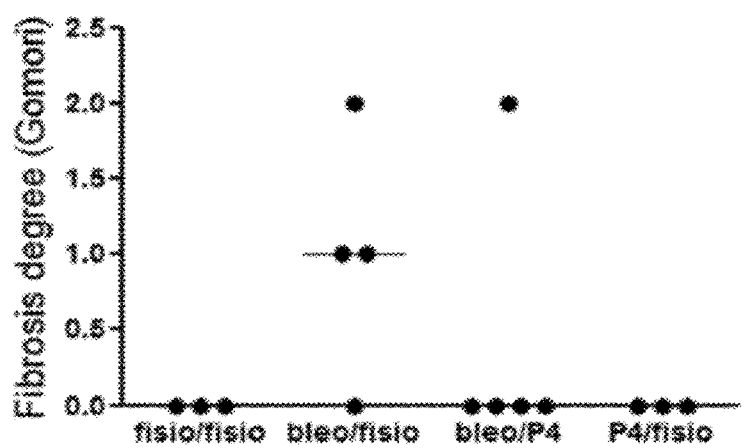
Figure 14:
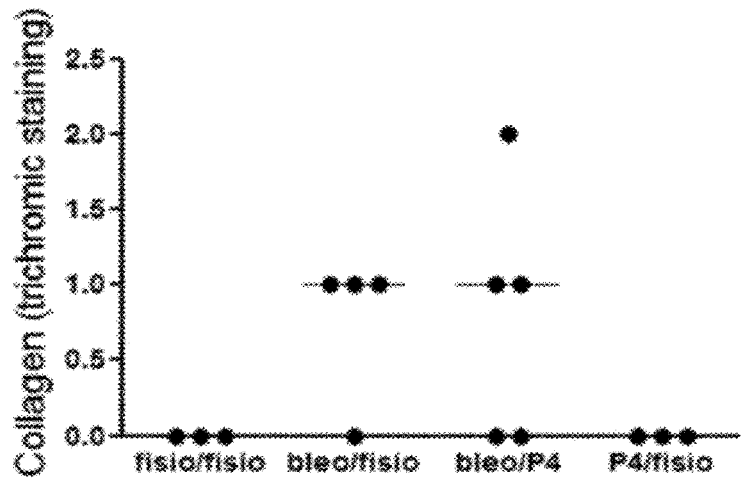

FIG. 14, frame A, B and C, shows the effect of P4E11 antibody on different parameters that are indicative of pulmonary fibrosis evaluated as described in Example 4, in mice treated with bleomycin (bleo/fisio), bleomycin associated with antibody (bleo/P4), antibody (P4/fisio) or saline alone (fisio/fisio), respectively.

Figure 15:
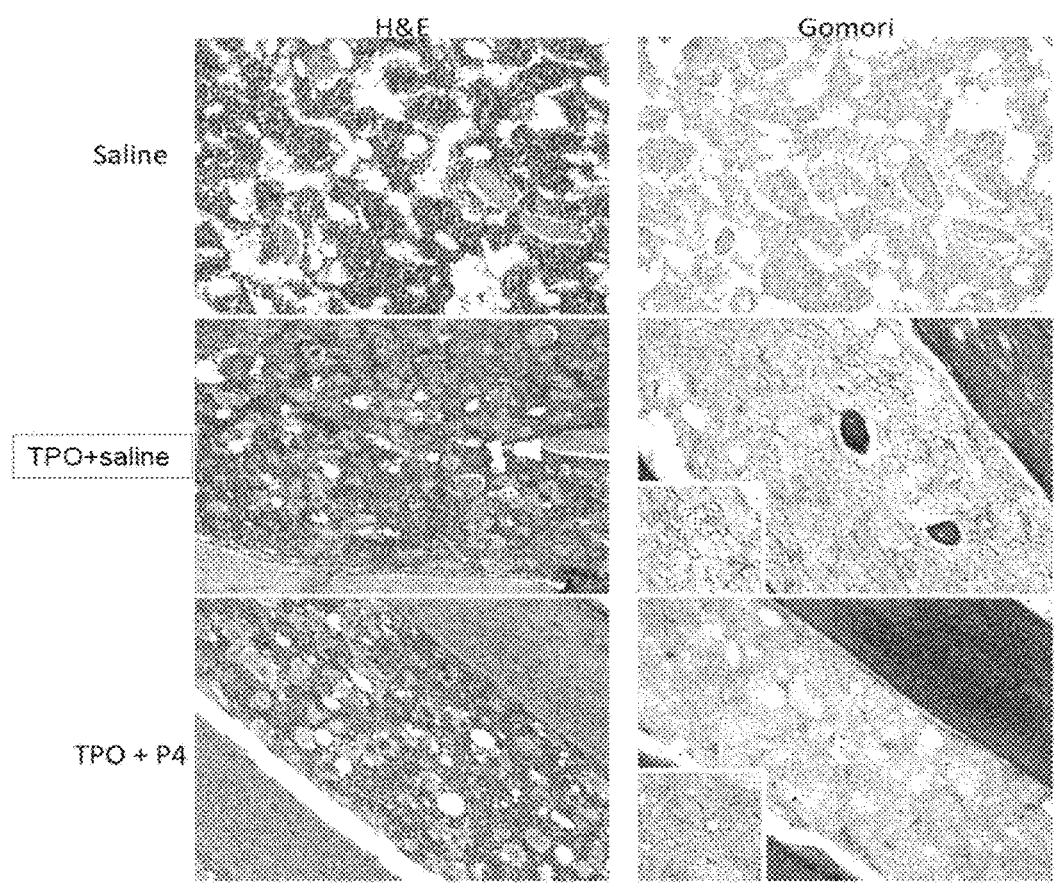

FIG. 15 shows histological sections of bone fragments, stained with Hemat/Eos (H&E) and Gomori (Gomori), of untreated mice (saline), or mice treated for 10 days with high doses of thrombopoietin (TPO+saline) or thrombopoietin associated with P4E11 antibody (TPO+P4).

Figure 16:
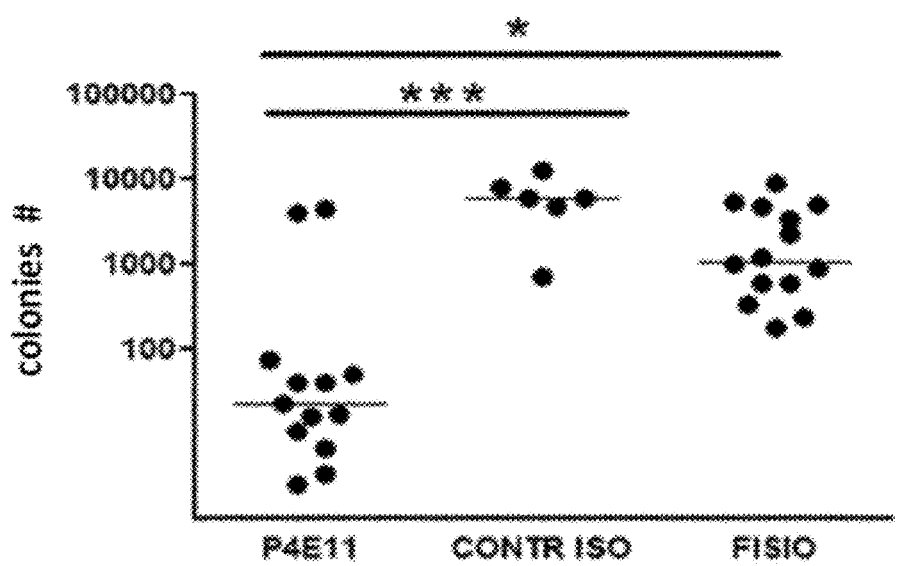

FIG. 16 shows the effect of P4E11 antibody on the formation of pulmonary metastases evaluated with a clonogenic test in mice treated (P4E11) or untreated (FISIO) with P4E11 or treated with an unrelated antibody of the same isotype (CONTR ISO), as described in Example 4. The ordinates show the number of thioguanine-resistant 4T1cl5 colonies, evaluated 15 days after the seeding of the cells derived from the animals' lungs. The differences between the groups evaluated with t-test were significant *(P=0.0457) and very significant ***(P=0.0003), respectively.

Figure 17:
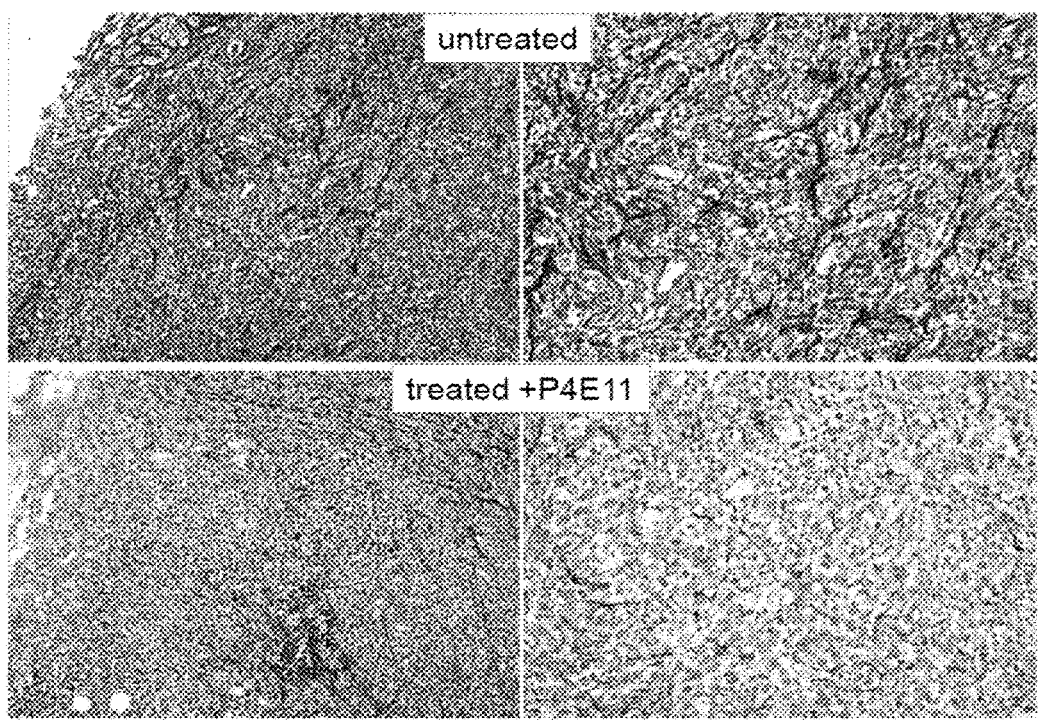

FIG. 17 shows two different magnified pictures of histological sections of primary 4T1cl5 tumor, untreated or treated with P4E11, as described in Example 4, after Gomori staining.

Figure 18:
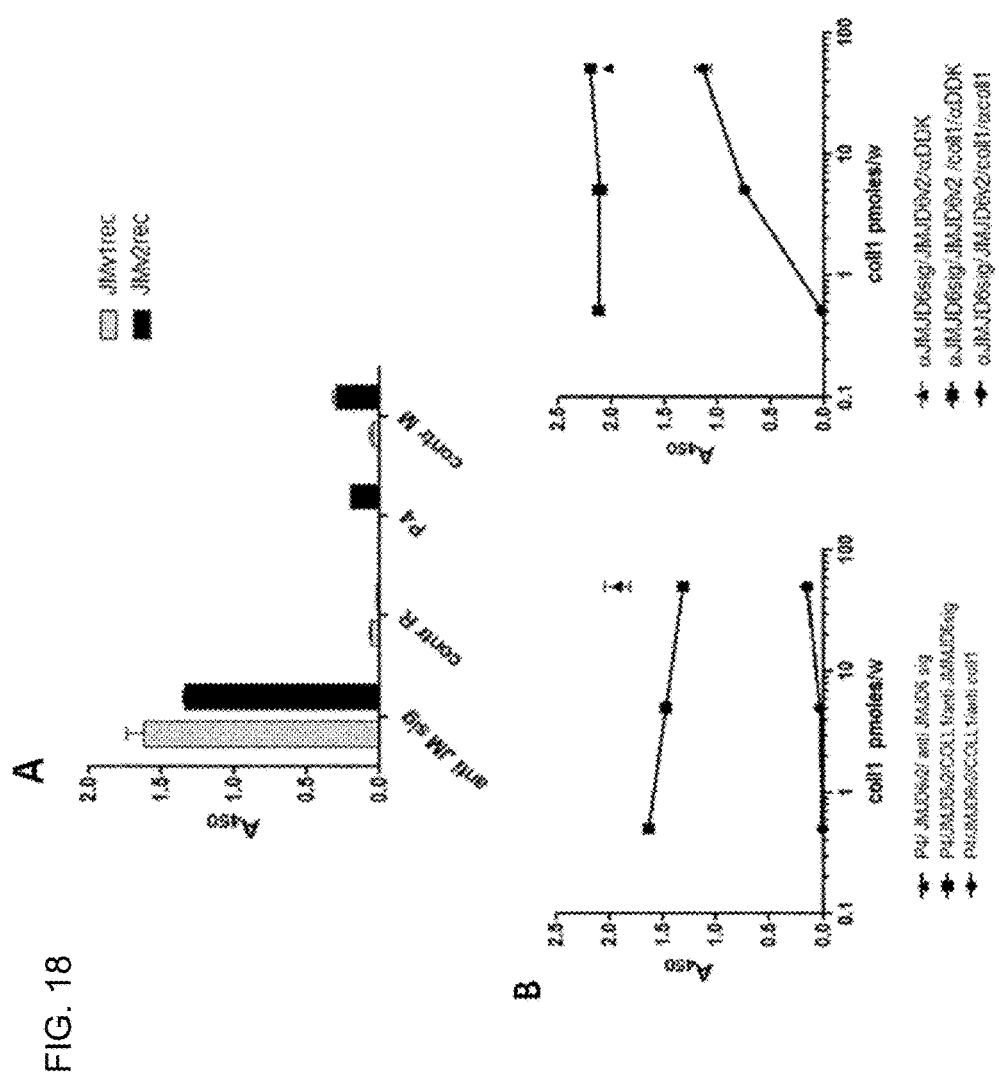

In FIG. 18, frame A, the ordinates show the absorbance values at 450 nm, which are indicative of the amount of complex between type-1 collagen (coll1) seeded in plates and JMJD6v1/v2rec, whereas the abscissas show the antibodies used for detecting this interaction: anti-JM sig (Sigma) and P4, and the negative controls (contr R for rabbit antibodies and contr M for mouse antibodies).

In frame B, left side, the ordinates show the absorbance values at 450 nm, which are indicative of the amount of recombinant JMD6v2 interacting with P4E11 antibody, if the binding is detected with αJMJD6 Sigma, in the absence (–▲–) or in the presence of (–■–) di coll1, or the amount of collagen which has interacted with JMJD6v2 rec, detected with an anti-coll1 antibody (–●–). In the same frame, right side, the ordinates show the absorbance values at 450 nm, which are indicative of the amount of recombinant JMJD6v2 interacting with αJMJD6 sigma antibody, if the binding is detected with anti-FLAG DDK, in the absence (–▲–) or in the presence (–■–) of coll1, or the amount of collagen which has interacted with JMJD6v2 rec, detected by an anti-coll1 antibody (–●–). In both graphs, the abscissas show the concentrations of coll1 expressed as pmoles/well (pmoles/w).

Figure 19:
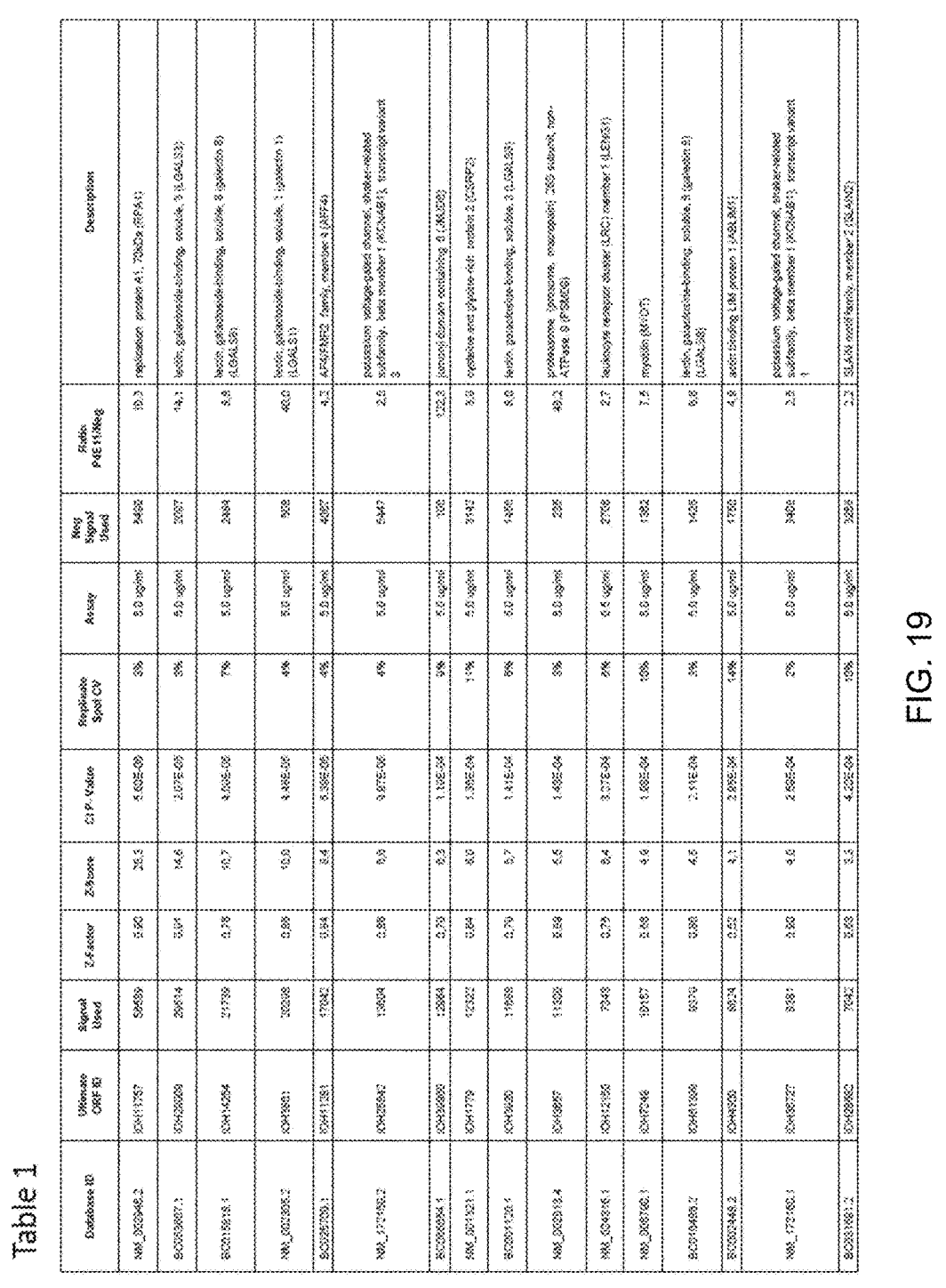

FIG. 19 shows data about the interaction of P4E11 antibody with 16 different proteins.

DETAILED DESCRIPTION OF THE INVENTION

As shall be discussed in further detail in Example 4 of the experimental part, the antibody identified by present inventors is able to inhibit fibrosis in normal or tumor tissues and the development of metastases, and is thus useful in the prevention and/or treatment of fibrosis and for the prevention and/or treatment of tumor metastases. Moreover, this activity is particularly relevant in antitumor treatment regimens, where the presence of a strong fibrotic component, produced both by microenvironment cells and by tumor cells themselves subjected to epithelial mesenchymal transition, can prevent the penetration of the chemotherapeutic drug into the tumor mass and as a result affects the efficacy of therapy.

As shall be discussed in Example 5 of the experimental part, the antifibrotic action of the antibody of the present invention derives from the inhibition of the interaction of JMJD6 with collagen.

The present inventors have identified the aminoacid sites on the JMD6 protein that are responsible for the binding with collagen. Furthermore, they have also found that compounds able to bind to two or more of these sites inhibit the interaction of JMJD6 with collagen.

Accordingly, a first object of the present invention relates to a compound that is able to block the interaction between collagen and JMJD6 protein wherein said compound binds to one or more portions of at least 5 consecutive amino acids of at least 2 of the following amino acid sequences of JMJD6 protein:

```
                                     (SEQ ID 33)
          RIREAKR, (SEQ ID 34)
          RKYRNQK, (SEQ ID 35)
          KMKYYIE, (SEQ ID 36)
          PKRRKLL, (SEQ ID 37)
          RPPYRWF, (SEQ ID 38)
          KRWCLFP, (SEQ ID 39)
          VPGGWWHVVLNLDTTIAITQN,
```

(SEQ ID 40)
VRGRPKLSR KWYRI, (SEQ ID 41)
HRRKKRR.

According to a preferred embodiment of the first object of the invention, said at least 2 sequences of JMJD6 protein comprise a sequence selected from KMKYYIE (SEQ ID 35) and KRWCLFP (SEQ ID 38), more preferably, both of these sequence. Even more preferably, the antibody also binds to one or more portions of 5 aminoacids of the sequence RSARPEL (SEQ ID 10).

According to a further preferred embodiment of the first object of the invention, also in combination with the previous embodiment, the above compound is selected from polyclonal antibodies and/or fragments thereof, monoclonal antibodies and/or fragments thereof, peptidomimetics, oligonucleotides and low molecular weight molecules. Preferably, said compound is a monoclonal antibody and/or a fragment thereof.

A preferred monoclonal antibody or antibody fragment according to the invention has variable regions of the light chains (VkCk) that comprise the following sequence (VkCk)
(SEQ ID 22)
NIMMTQSPSSLAVSAGEKVTMNCKSSQSILYSSNHKNYLAWYQQKPGQSP

KLLIYWASTRESGVPNRFTGSGSGTDFTLTISSVQSEDLAVYYCHQYLSS

YTFGGGTKLEIKRADAAPTVSIFPPSSEQLTSGGASVVCFLNNFYPKDIN

VKWKIDGSERQNGVLNSWTDQDSKDSTYSMSSTLTLTKDEYERH.

A further preferred monoclonal antibody or antibody fragment according to the invention has variable regions of the heavy chains (VkCh) that comprise the following sequences (VhCh)
(SEQ ID 23)
QVQLKQSGPGLVQPSQSLSITCTVSGFSLSSYGVHWVRQSPGKGLEWLGV

IWRSGNTDYNAVFMSRLSITKDDSKSQVFFKMNSLQADDTAIYYCAKNFR

YDVGSWFAYWGQGTLVTVSAAKTTAPSVYPLAPVCGDTTGSSVTLGCLVK

GYFPEPVTLTWNSGSLSSGVHTFPAVLQSDLYTLSSSVTVTSSTWPSQSI

TCNVP
or (VhCh)
(SEQ ID 32)
QVQMKQSGPGLVQPSQSLSITCTVSGFSLSSYGVHWVRQSPGKGLEWLGV

IWRSGNTDYNAVFMSRLSITKDDSKSQVFFKMNSLQADDTAIYYCAKNFR

YDVGSWFAYWGQGTLVTVSAAKTTAPSVYPLAPVCGDTTGSSVTLGCLVK

GYFPEPVTLTWNSGSLSSGVHTFPAVLQSDLYTLSSSVTVTSSTWPSQSI

TCNVP.

Even more preferably said monoclonal antibody or antibody fragment according to the invention has variable regions of the light chains (VkCk) that comprise the following sequence (VkCk)
(SEQ ID 22)
NIMMTQSPSSLAVSAGEKVTMNCKSSQSILYSSNHKNYLAWYQQKPGQSP

KLLIYWASTRESGVPNRFTGSGSGTDFTLTISSVQSEDLAVYYCHQYLSS

YTFGGGTKLEIKRADAAPTVSIFPPSSEQLTSGGASVVCFLNNFYPKDIN

VKWKIDGSERQNGVLNSWTDQDSKDSTYSMSSTLTLTKDEYERH and/or
variable regions of the heavy chains (VkCh) that comprise the following sequences (VhCh)
(SEQ ID 23)
QVQLKQSGPGLVQPSQSLSITCTVSGFSLSSYGVHWVRQSPGKGLEWLGV

IWRSGNTDYNAVFMSRLSITKDDSKSQVFFKMNSLQADDTAIYYCAKNFR

YDVGSWFAYWGQGTLVTVSAAKTTAPSVYPLAPVCGDTTGSSVTLGCLVK

GYFPEPVTLTWNSGSLSSGVHTFPAVLQSDLYTLSSSVTVTSSTWPSQSI

TCNVP
or (VhCh)
(SEQ ID 32)
QVQMKQSGPGLVQPSQSLSITCTVSGFSLSSYGVHWVRQSPGKGLEWLGV

IWRSGNTDYNAVFMSRLSITKDDSKSQVFFKMNSLQADDTAIYYCAKNFR

YDVGSWFAYWGQGTLVTVSAAKTTAPSVYPLAPVCGDTTGSSVTLGCLVK

GYFPEPVTLTWNSGSLSSGVHTFPAVLQSDLYTLSSSVTVTSSTWPSQSI

TCNVP.

Preferably said antibody is a monoclonal antibody, or a fragment thereof, deriving from the hybridoma deposited with the Autorità Internazionale di Deposito (AID) Centro di Biotecnologie Avanzate (CBA)—Interlab Cell Line Collection (ICLC) of Genoa (Italy), access number PD 15001, deposited on Jan. 13, 2015, and available from IRCCS Azienda Ospedaliera Universitaria San Martino IST Istituto Nazionale per la Ricerca sul Cancro, L. go R. Benzi, 10, 16132 GENOVA, ITALY.

As shall be described in Example 2 of the experimental part, the P4E11 antibody produced by the present inventors, contrary to prior-art anti-JMJD6 antibodies, recognizes a conformational epitope of JMJD6, sensitive to heat denaturation. As demonstrated by data shown in FIG. 5, frame A and B, this antibody can bind specifically to the protein in its native conformation and not to linear peptides of the protein itself. These data are confirmed by the fact that the epitope is only recognized on the complete protein and not in protein fragments corresponding to the N portion or C terminus thereof. As demonstrated by data shown in FIG. 6, frame A and C, the whole protein sequence is necessary to maintain the conformation recognized by the antibody of the present invention.

Therefore, a second object of the present invention relates to a monoclonal antibody, or a fragment thereof, against JMJD6 protein, characterized in that this antibody binds only to said protein in its native conformation and not in its heat-denaturated conformation or to linear peptides of the protein itself
and/or
this antibody recognizes a heat-sensitive conformational epitope, preferably it recognizes the epitope consisting of an amino acid sequence comprising one or more portions of at least 5 amino acids of at least 2 of the following amino acid sequences of said protein:

RIREAKR, (SEQ ID 33)

RKYRNQK, (SEQ ID 34)

KMKYYIE, (SEQ ID 35)

PKRRKLL, (SEQ ID 36)

RPPYRWF, (SEQ ID 37)

KRWCLFP, (SEQ ID 38)

VPGGWWHVVLNLDTTIAITQN, SEQ ID 39)

VRGRPKLSR KWYRI, (SEQ ID 40)

HRRKKRR. (SEQ ID 41)

Preferably, according to the second object of the invention, said at least 2 sequences of JMJD6 protein comprise a sequence selected from

KMKYYIE; (SEQ ID 35)

KRWCLFP. (SEQ ID 38)

More preferably, according to said embodiment of the second object of the invention, said at least 2 sequences of JMJD6 protein comprise both the sequences

KMKYYIE; (SEQ ID 35)

KRWCLFP. (SEQ ID 38)

Most preferably, according to the second object of the invention, said at least 2 sequences of JMJD6 protein comprise both the sequences

KMKYYIE; (SEQ ID 35)

KRWCLFP (SEQ ID 38)

and the monoclonal antibody, or fragment thereof, binds also to one or more portions of 5 aminoacids of sequence RSARPEL (SEQ ID 10).

According to a preferred embodiment of the second object of the invention, said monoclonal antibody, or a fragment thereof, derives from the hybridoma deposited with the Autorità Internazionale di Deposito (AID) Centro di Biotecnologie Avanzate (CBA)—Interlab Cell Line Collection (ICLC) of Genoa (Italy), access no. PD 15001. Methods to develop and/or to identify compounds, preferably monoclonal antibodies, that bind the amino acid sequences claimed are known to the expert in the art; for example, it is possible to produce monoclonal antibodies (mAb) recognizing specific aminoacid sequences. The way to produce monoclonal antibodies stems are, for example, classical hybridoma technology (Köhler G, Milstein C. Continuous cultures of fused cells secreting antibody of predefined specificity. Nature. 1975, 256:495-7.), recombinant mAb technologies, referred to as phage display/yeast display (McCafferty et al. Nature. 1990 348:552-4) or transgenic mice technology, which is suitable for making "fully" human monoclonal antibodies (Brüggemann M. et al. Human antibody production in transgenic animals. Arch. Immunol. Ther. Exp. 2015, 63:101-108). Furthermore, phage display technology of random peptides libraries allows selection of biologically active peptides binding to certain amino acid sequences (Cortese r. et al. Selection of biologically active peptides by phage display of random peptides libraries. Curr. Opin. Biotechnol., 1996, 7:616-621).

A third object of the present invention relates to the above compound or monoclonal antibody for use as a medicament.

A fourth object of the present invention is the above compound or monoclonal antibody for use in the prevention and/or treatment of fibrosis.

According to a preferred embodiment of the fourth object of the invention, preferably said compound or monoclonal antibody is for use in the prevention and/or treatment of pulmonary, peritoneal (due for instance to surgery treatments), medullary (also known as myelofibrosis) and tumor tissue fibrosis.

A fifth object of the present invention is the above compound or monoclonal antibody for use in the prevention and/or treatment of tumor metastases.

According to a preferred embodiment of the fifth object of the invention, preferably said compound or monoclonal antibody is for use in the prevention and/or treatment of metastases deriving from mammary or ovarian cancer.

A sixth object of the present invention is the above compound or monoclonal antibody for use in association with radiotherapy and/or chemotherapy in the treatment of a tumor.

According to one embodiment of the sixth object of the present invention, preferably said compound or antibody is used in association with radiotherapy and/or chemotherapy in the treatment of specific tumor types including, though not limited, to, bladder cancer, mammary cancer, colon cancer, kidney cancer, liver cancer, lung cancer, including small cell lung tumor, esophageal cancer, gallbladder cancer, ovarian cancer, pancreas cancer, stomach cancer, cervical cancer, thyroid cancer, prostate cancer and skin cancer, among which squamous cell carcinoma; hematopoietic tumors of the lymphoid lineage among which acute lymphatic leukemia, acute lymphoblastic leukemia, B-cell lymphoma, T-cell lymphoma, Hodgkin lymphoma, non-Hodgkin lymphoma, hairy cell lymphoma and Burkitt lymphoma; hematopoietic tumors of the myeloid lineage, among which acute and chronic myeloid leukemias, myelodysplastic syndrome and promyelocitic leukemia; tumors of mesenchymal origin, including fibrosarcoma and rhabdomyosarcoma; tumors of the central and peripheral nervous system, among which astrocytoma, neuroblastoma, glyomas and neurinomas; other tumors, including melanoma, seminoma, teratocarcinoma, osteosarcoma, xeroderma pigmentosum, keratoxanthoma, follicular thyroid carcinoma and Kaposi sarcoma.

A seventh object of the present invention is a pharmaceutical composition comprising the above compound or antibody, and at least one pharmaceutically acceptable carrier and/or excipient.

Particularly preferred pharmaceutical forms of the invention are those suitable for injectable use, in particular for intravenous or intraperitoneal infusion and include sterile aqueous solutions (where water soluble) or sterile dispersions or sterile powders for the extemporary preparation of sterile injectable solutions and/or dispersions and one or more excipients. As an alternative, injectable solutions can be delivered encapsulated into liposomes in order to make their transport through the cell membrane easier. As an alternative or in addition, these preparations can contain self-assembling porous components in order to make the transport through the cell membrane easier. These forms should be stable in manufacturing and storage conditions and should be preserved against the contaminating/destroying action of microorganisms such as e.g. bacteria and fungi.

The carrier can be a solvent or a dispersion medium containing e.g. water, ethanol, polyol (e.g. glycerol, propylene glycol and liquid polyethylene glycol, and the like), suitable mixtures thereof and vegetable oils. The correct fluidity can be preserved e.g. by using a coating such as e.g. lecithin, for preserving the particle size required for dispersions and by using surfactants. In order to prevent the action of microorganisms in the compositions of the invention, an antibacterial agent and/or an antifungal agent can be added, e.g. parabens, chlorobutanol, phenol, sorbic acid, thimerosal and the like. In many cases, it will be preferred to include an isotonic agent, e.g. sugars or sodium chloride. A prolonged absorption of the injectable compositions can be obtained by using in the compositions agents such as e.g. aluminum monostearate and gelatin so as to delay absorption.

The sterile injectable solutions are prepared by incorporating the active compounds in a necessary amount into the suitable solvent with some of the other ingredients listed above, as required, followed by filtered sterilization. Generally, the dispersions are prepared by incorporating the various sterilized active agents into a sterile carrier containing the basic dispersion medium and the other required ingredients among those listed above. In the case of sterile powders for preparing sterile injectable solutions, the preferred methods of preparation are drying under vacuum and freeze-drying, so as to obtain a powder of the active agent and any desired complementary ingredient from the previously filtered, sterile solution.

It is particularly advantageous to formulate parenteral compositions as a unitary dosage form for a simple administration and dosage uniformity. The wording "unitary dosage form" as used herein refers to physically discrete units that are suitable as unitary dosages for the mammals to be treated, each unit containing a predefined amount of active material calculated so as to obtain the desired therapeutic effect in association with the required pharmaceutical carrier. The unitary dosage forms of the invention are dictated by and depend directly on the unique characteristic/s of the active material and the particular therapeutic effect to be achieved, and (b) the technique-intrinsic limitations so as to formulate this active material for the treatment of the disease in living subjects having a disease condition in which the body's health is endangered as described here in detail.

The main active ingredient is formulated for a comfortable and effective administration in effective amounts with a suitable, pharmaceutically acceptable carrier in a unitary dosage form. A unitary dosage form can contain e.g. the antibody of the invention in amounts between 1 and 10 mg/kg. In the case of formulations containing additional active ingredients, the dosages thereof are determined referring to the usual dose and administration route of said ingredients.

An eighth object of the present invention relates to combination of the above compound or antibody with at least one chemotherapeutic drug.

Preferably, said chemotherapeutic drug is selected from cytostatic and cytotoxic agents, antibiotics, alkylating agents, antimetabolites, hormonal agents, immunologic agents, interferon-like agents, inhibitors of cyclooxygenase, inhibitors of matrix metalloproteases, inhibitors of telomerase, tyrosine kinase inhibitors, inhibitors of growth factors, anti-receptors agents of HER family, anti-EGFR agents, anti-angiogenesis agents (inhibitors of angiogenesis), farnesyl transferase inhibitors, inhibitors of the transduction of ras-raf signal, inhibitors of cellular cycle, other cdks inhibitors, tubulin binding agents, inhibitors of topoisomerase I and II and the like.

Preferably, said known chemotherapeutic drug is selected from bleomycin, fludarabine and methotrexate.

A ninth object of the present invention relates to the above combination for use in the treatment of a tumor.

Preferably, said tumor is selected from bladder cancer, mammary cancer, colon cancer, kidney cancer, liver cancer, lung cancer, including small cell lung tumor, esophageal cancer, gallbladder cancer, ovarian cancer, pancreas cancer, stomach cancer, cervical cancer, thyroid cancer, prostate cancer and skin cancer, among which squamous cell carcinoma; hematopoietic tumors of the lymphoid lineage among which acute lymphatic leukemia, acute lymphoblastic leukemia, B-cell lymphoma, T-cell lymphoma, Hodgkin lymphoma, non-Hodgkin lymphoma, hairy cell lymphoma and Burkitt lymphoma; hematopoietic tumors of the myeloid lineage, among which acute and chronic myeloid leukemias, myelodysplastic syndrome and promyelocitic leukemia; tumors of mesenchymal origin, including fibrosarcoma and rhabdomyosarcoma; tumors of the central and peripheral nervous system, among which astrocytoma, neuroblastoma, glyomas and neurinomas; other tumors, including melanoma, seminoma, teratocarcinoma, osteosarcoma, xeroderma pigmentosum, keratoxanthoma, follicular thyroid carcinoma and Kaposi sarcoma.

A tenth object of the present invention relates to a hybridoma for the production of the above compound wherein the compound is a monoclonal antibody. Preferably, the hybridoma is the one deposited with the Autorità Internazionale di Deposito (AID) Centro di Biotecnologie Avanzate (CBA)—Interlab Cell Line Collection (ICLC) of Genoa (Italy), access no. PD 15001.

An eleventh object of the present invention relates to the hybridoma deposited with the Autorità Internazionale di Deposito (AID) Centro di Biotecnologie Avanzate (CBA)—Interlab Cell Line Collection (ICLC) of Genoa (Italy), access no. PD 1500.

An twelfth object of the present invention relates to an antibody obtained from an hybridoma as defined above.

A thirteenth object of the present invention relates to a method for the prevention and/or treatment of a disease selected from fibrosis and tumor metastases in a patient by administering a compound or a monoclonal antibody as defined above in a pharmaceutically effective amount in order to prevent and/or treat this disease.

A thirteen object of the present invention relates to a method for treating tumors in a patient by administering a compound or a monoclonal antibody as defined above in a pharmaceutically effective amount in association with radiotherapy and/or chemotherapy.

Experimental Part
Materials and Methods
Cell Lines
The following murine cell lines were used:
Normal fibroblasts BALB/c (Fibro wt) and normal fibroblasts Sparc–/– (Fibro Sparc KO) (Sangaletti et al. *SPARC*

*oppositely regulates inflammation and fibrosis in bleomycin induced lung damage. Am J Pathol* 2011. 179: 3000-10);

the mammary cancer line SN25a; the mammary cancer line 4T1, resistant to thioguanine (Aslakson C J, Miller F R., *Selective events in the metastatic process defined by analysis of the sequential dissemination of subpopulations of a mouse mammary tumor*, Cancer Res 1992; 52: 1399-405) (CRL-2539, LGC-Promochem) and, where specified, a clone thereof referred to as 4T1c15, selected in our laboratory;

the stromal line AFT024 (Moore et al., *In vitro maintenance of highly purified, transpalantable hematopoietic stem cells. Blood* 1997; 89: 4334-47), (ATCC) and the macrophage-derived line RAW264.7 (ATCC, TIB-71). Moreover, the following human tumor lines are used: mammary cancer MDAMB231 (ATCC, HTB-26), MCF7 (ATCC, HTB-22) and SKBR3 (ATCC, HTB30);

ovarian cancer lines SKOV3 (ATCC, HTB-77) and IGROV1 (Tessier J et al., *Drug-related chromosomal changes in chemo resistant human ovarian carcinoma cells. Cancer Genet Cytogenetic* 1989 May; 39(1):35-43); melanoma lines MeWo (ATCC, HTB-65), A375M (Kozlowski et al. *Metastatic behavior of human tumor cell lines grown in the nude mice. Cancer Res* 1984; 44:3522-3529); Mel 665.1 (Anichini et al., *Cytotoxic T lymphocyte clones from peripheral blood and from tumor site detect intratumor heterogeneity of melanoma cells. Analysis of specificity and mechanisms of interaction. J Immunol* 1989; 142 (10): 3692-701); the line of promyelocitic leukemia U937 (Larrick J W, *Characterization of a human macrophage-like cell line stimulated in vitro: a model of macrophage functions. J Immunol* 1980. 125(10): 6-12) and of T-leukemia Jurkat (ATCC, CRL-1593.2).

Murine cell lines were cultured in D-MEM (Lonza) and human cell lines in RPMI-1640 (Gibco-Life technologies) containing 1% glutamine and 10% fetal bovine serum (FBS) (PAA laboratories), at 37° C. in the presence of 5% $CO_2$.

Reagents and Antibodies

All the reagents were of highly purified grade and, if not otherwise specified, produced by Sigma. The following purified proteins were used: recombinant JMJD6 [Origene, variant 1 (v1), #TP 318163 and variant 2 (v2) #TP308993], type 1 collagen (coll1) (BD, #354236), type 4 collagen (coll4) (Sigma, #C0543), plasmatic fibronectin (pFN) (Sigma, #F4759) and cellular fibronectin (cFN) (Sigma, #F2518). The following commercial anti-JMJD6 antibodies were used: a) polyclonal rabbit antibody (Sigma, #P1495), b) polyclonal rabbit antibody (Abcam, #ab64575), c) polyclonal rabbit antibody (Abnova, #PAB2219), d) monoclonal mouse antibody (Santa Cruz, #sc-28348); monoclonal mouse anti-DDK antibody (Origene, #TA50011) which recognizes a FLAG epitope expressed on recombinant JMJD6 proteins; polyclonal rabbit anti-coll1 antibody (Millipore, #AB765P); monoclonal mouse anti-coll1 antibody (Sigma, #C2456); monoclonal mouse anti-CD63 antibody (Abcam, #8219); monoclonal mouse anti-GAPDH antibody (Sigma, #G8795); purified mouse antibodies of gamma 2a and gamma 1 class, used as isotype controls (Cerdelane, #CLCMG2A00 and #CLX500AP); purified normal mouse and rabbit IgGs (Santa Cruz, #2025 and #2027), polyclonal rabbit anti-DDK-Alexa fluor 488 antibody (Cell Signaling, #5407).

Mice

BALB/c, Nude and SCID mice, aged 5-7 weeks, were supplied by Charles River. All treatments on animals were authorized by the Institutional Ethics Committee.

Immunofluorescence and FACs Analysis

In order to assay the expression of intracellular proteins, cells were detached with trypsin, fixed with 4% paraformaldehyde and permeabilized with 0.5% saponin. After saturation in the presence of 1% FBS, cells were incubated at room temperature with the primary P4E11 antibody, then with the secondary biotinylated antibody (GE-Helthcare) and with streptavidin—Alexa488 (Invitrogen). All the buffers used for permeabilization, reagent dilutions and washing contained 0.5% saponin and 1% FBS. The cytofluorimetric analysis was performed with Fortessa (Becton Dickinson) using as control cells incubated with the secondary antibody and streptavidin-Alexa488 only or an unrelated antibody of the same isotype γ2a (isotype control).

Immunofluorescence on Adhering Cells

The cells (25-40,000) were sown onto a slide and grown for at least 48 hours. For the analysis of membrane expression they were fixed in 2% PFA for 20 minutes at room, for the intracellular analysis after fixation in PFA they were permeabilized with 0.1% Triton x-100. After saturation in 1% PBS-BSA the cells were incubated with the primary and secondary antibodies marked with fluorochrome (Alexa Fluor, Molecular Probes, Invitrogen). The nuclei were stained with DRAQS (Molecular Probes-Invitrogen). The stained cells were analyzed with a confocal microscope RADiance-2000 (BioRad). The pictures correspond to a central section on Z axis.

Histology and Immunohistochemistry

All tissues were fixed in formalin immediately after being removed and incorporated into paraffin. For the morphological analysis the lungs were fixed in-situ, after sacrificing the animal, by means of intratracheal inoculation of buffered formalin, then removed and left in formalin for 24 hours. The histopathological analysis was performed in 4 μm sections stained with hematoxylin and eosin, Gomori reticulin staining, and Masson trichrome staining. The immunohistochemical analysis of human tumor samples was performed on sections subjected to antigen unmasking in Tris-EDTA buffer pH 9. The staining was developed with the streptavidin-biotin-peroxidase method.

Preparation of Cell Lysates for Western Blot Analysis and Immunoprecipitation

After 2 washing cycles in PBS, the adhering cells were lysated in a flask with a lysis buffer [50 mm Tris-HCl pH 7.4+150 mM NaCl, 1% NP-40, 0.1% SDS, cocktail of inhibitors of proteases (Roche), 1 mM PMSF, cocktail of inhibitors of phosphatase (Phosphostop, Roche), 1 mM $Na_3VO_4$] for 30-40 minutes in ice. The lysate was centrifuged for 15 minutes at 13,000 rpm, the supernatant was recovered and dosed for the protein content with BCA method (Pierce). For Western Blot analyses, the cell lysates were separated in SDS-PAGE on gel NuPAGE mini gels 4-12% (Invitrogen) and transferred onto a nitrocellulose membrane (GE). After saturation in 5% milk in PBS+0.1% Tween 20 (blot) for 1 hour, the immunoreactions were performed with the primary (1 hour) and secondary peroxidase-conjugated antibodies (30 minutes) and the reaction was developed with ECL (GE Health Care) or ECL plus (Pierce). For the immunoprecipitation, the cell lysates were incubated with P4E11 or with an unrelated antibody of the same isotype, directly conjugated with magnetic beads (Dynabeads) epoxy-activated according to the method indicated by the manufacturer (Dynal). For commercial antibodies magnetic beads that are already conjugated with anti-immunoglobulin mouse or rabbit antibodies were used. All beads were saturated in 0.1% PBS+ BSA and then incubated with the cell lysates for 3 hours under rotation at 4° C. After 4 washing cycles in PBS-0.1% Triton X-100, the immunoprecipitates were dissociated with 3 M NaSCN for 2 mins at room temperature, or in NuPAGE LDS sample buffer 1× at 95° C. for 5 minutes, separated from the beads by means of a magnet, recovered and treated or not with reducing agent for 5 minutes at 95° C. and then analyzed in Western Blot. As an alternative to cell lysates, human purified recombinant JMJD6 proteins in both variants (v1 and v2) were used, having a FLAG (DDK) sequence at C terminus.

Elisa

In order to assay the presence of JMJD6 in cell lysates an immunoenzymatic assay was used, in which an anti-JMJD6 antibody (A) was adhered to a plate and a second antibody (B), produced in a different species, was used in soluble form for detecting the occurrence of the interaction of the antigen with the first antibody, The test was initially validated using recombinant JMJD6 protein with P4E11 as antibody in the plate and anti-JMJD6 (polyclonal rabbit antibody by Sigma) as antibody in soluble form. Then other combinations of anti-JMJD6 antibodies were assayed, including the anti-FLAG antibody which is able to recognize the DDK epitope expressed on the recombinant protein. Antibody A (1 ug/well in PBS) was adhered to the plate (whole night at 4° C.), the following day the plate was saturated with 1% BSA in PBS, then incubated with the antigen source (recombinant protein) for 1 h, followed by incubation for 1 h with antibody B and then with the secondary peroxidized antibody. After adding the substrate (TNB, Sigma) the reaction was stopped with 1N $H_2SO_4$ and the plate read at 450 nm. All incubations were at room temperature.

Elisa on ECM Proteins

Purified extracellular matrix proteins (coll1, coll4, pFN, cFN) were seeded in a plate in 50 pmoles/well scalar doses and incubated for the whole night at 4° C. BSA at the same doses was seeded as a control. The following day the wells were saturated with 1% BSA and then incubated with purified recombinant JMJD6 (10 nM) for the whole night at 4° C. The occurrence of the interaction was detected with an anti-JMJD6 or anti-DDK antibody (1 ug/ml-1 h at room T) followed by the required secondary peroxidase-conjugated antibody (1 h a room T). The reaction was developed and read at 450 nm as indicated above.

Elisa on JMJD6 Peptides

A peptide library was synthesized (Primm), consisting of 57 peptides with 14 amino acids each and whose sequences overlap for 7 amino acids. In order to assay the interaction with collagen, the peptides, were sown in a plate (1 ug/well) and incubated for the whole night at 4° C. The following day the wells were saturated with 1% BSA and incubated for 1 h at room T with coll1 (50 pmoles/well). In order to detect the possible interaction, a monoclonal anti-coll1 antibody (1 ug/ml-1 h at room T) was used, followed by the required secondary peroxidase-conjugated antibody (1 h at room T). The reaction was developed and read at 450 nm as indicated above. As control two unrelated peptides were used and the reactivity of the antibodies on the peptides in absence of collagen was evaluated. The reactivity of P4E11 and of the polyclonal anti-JMJD6 antibody (Sigma) was evaluated on peptides seeded in the plate as indicated above and detected with the required secondary peroxidized antibodies.

Epitope Mapping of JMJD6-P4E11

1 µg of JMJD6v2rec alone; 1 µg of JMJD6v2rec+37.5 µg P4E11; 1 µg of JMJD6v2rec+37.5 µg W6 (unrelated Ab) were digested with trypsin (Roche Diagnostics) (w/w=50:1) or endoproteinase Glu-C (Roche Diagnostics) (w/w=50:1) in ammonium hydrogen carbonate 50 mM pH=7 at 37° C. for 3 h or 6 h, respectively. Upon digestion, peptides were desalted using a C18 stage tip and separated on a homemade 12-cm reverse phase spraying fused silica capillary column (75 µm i.d.), packed with 1.9-µm ReproSil 120 Å C18 (Dr. Maisch GmbH, Germany). A gradient of eluents A (pure water, 0.1% v/v formic acid) and B (ACN with 0.1% v/v formic acid) was used to achieve separation, from: 0% B (0.3 µL/min flow rate) to 45% B in 45 minutes by nUPLC (Easy 1000 nLC, Proxeon Biosystem, Denmark) coupled to the Q-Exactive mass spectrometer (Thermo Scientific, Bremen, Germany) equipped with a nano-electrospray ion source (Proxeon Biosystems, Odense, Denmark). Full scan mass spectra were acquired in the Q-Exactive mass spectrometer with the resolution set to 35,000. For accurate mass measurements the lock-mass option was used. The acquisition mass range for each sample was from m/z 300 to 2000 Da. The ten most intense doubly and triply charged ions were automatically selected and fragmented in the orbitrap after accumulation to a 'target value' of 100,000. Target ions already selected for the MS/MS were dynamically excluded for 15 s. All MS/MS samples were analyzed using Mascot search engine (version 2.2.07, Matrix Science, London, UK) and X! Tandem search engine (within Scaffold version 3.6.4, Proteome Software Inc., Portland, Oreg.) to validate MS/MS based peptide and protein identifications. Protein thresholds were set to 99.0% minimum and two peptides minimum while peptide thresholds were set to 95% minimum. X! Tandem and Mascot were set up to search the UniProtK-B_Human complete proteome_2015_04 database (total 90411 sequences). For Q-Exactive data, mass tolerance was set to 5 ppm and 0.3 Da for precursor and fragment ions, respectively. Searches were performed with trypsin or Glu-C specificity, 5 missed cleavages, no alkylation of cysteine, oxidation of methionine and acetylation on N-terminal protein as variable modifications.

By differential mapping of JMJD6v2rec alone; JMJD6v2rec+P4E11; JMJD6v3rec+W6, the specific epitope on JMJD6 recognized by P4E11 was defined.

Preparation of Constructs for the Stable Expression of JMJD6 and Transfection cDNA of JMJD6 variant 1 (Origene, #SC315948) and of JMJD6 variant 2 ((Origene, #127976), which differ one from the other for the presence or absence, respectively of 33 bp coding 11 amino acids in C terminus, was extracted from the vector pCMV6-XL4 and re-cloned into vector pcDNA3 (Invitrogen).

Figure 6:
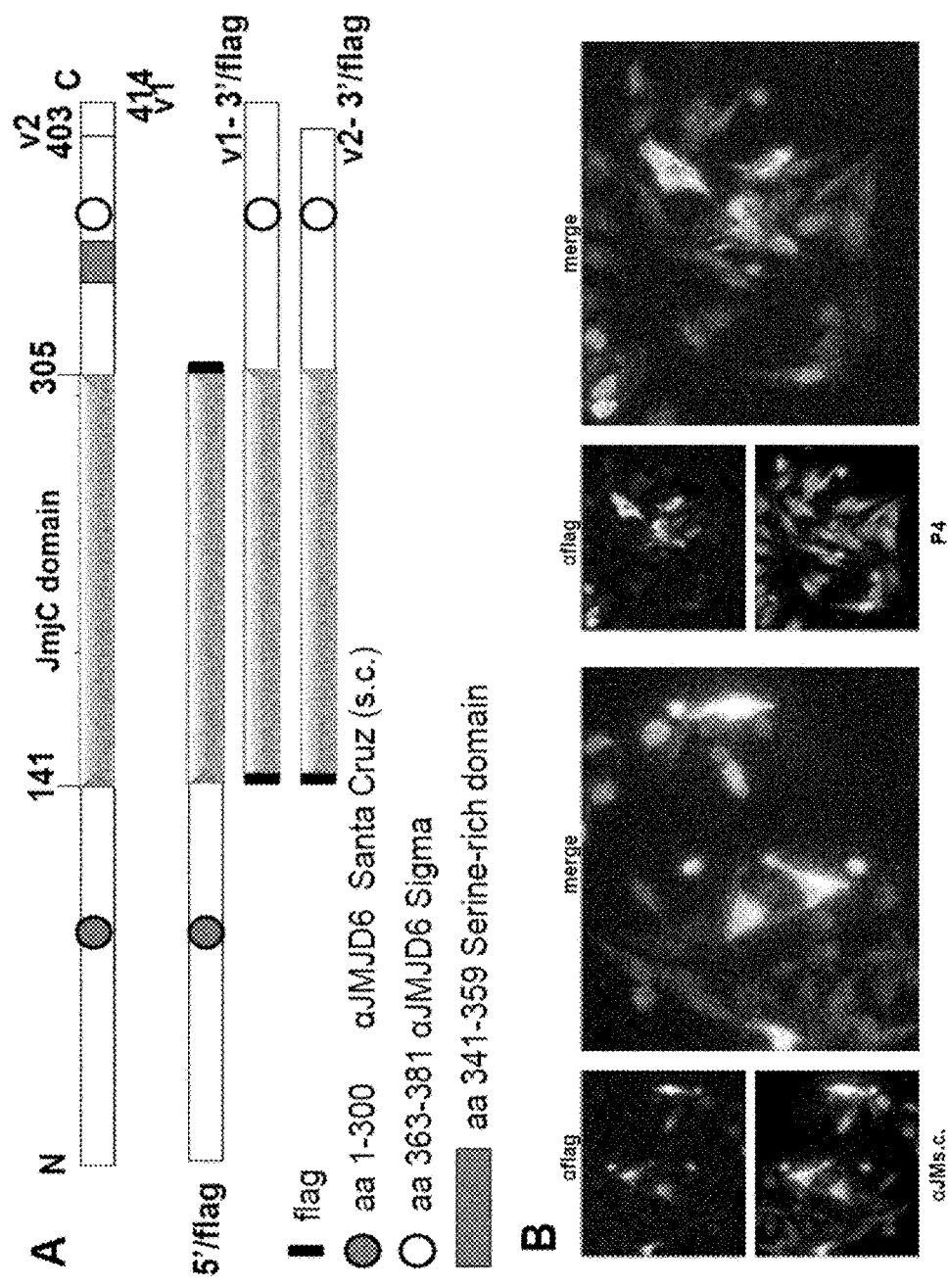
FIG. 6 shows in frame A the two human variants (v1 and v2) of JMJD6 and the proteins deriving therefrom, lacking the sequences downstream (5'/FLAG) or upstream (v1 3'/FLAG and v2 3'/FLAG), respectively, from the region with enzymatic activity, where the positions of the epitopes recognized by the commercial anti-JMJD6 antibodies Santa Cruz and Sigma are indicated.

Moreover, 3 constructs of JMJD6 were prepared, all including the JmjC domain, comprising amino acids 141 to 305 of JMJD6 flanked by a FLAG N or C-terminal sequence, as described in FIG. 6.

The fragment of JMJD6 at 5' (amino acids 1-305, being the same in both variants it shall be referred to as 5'/FLAG) with 941 bp was amplified by PCR using as primers

```
JMJD6 5' Forward (F)
                                           (SEQ ID 24)
(5'-CTGCAGAAGCTTGCGGAACCAGCTGGCGACCCCGC-3')
and JMJD6 5' + FLAG Reverse (R)
                                           (SEQ ID 25)
(5'CTGCAGTCTAGACCTTATCGTCATCGTCCTTGTAGTCTCTCCCTCTT

ACCGTCTTGTGCC-3')
``` and then cloned into vector pcDNA3. Primer R contains a DDK (FLAG) sequence in frame with JMJD6 sequence.

The fragment with 834 bp (JMJD6 v1-3'/FLAG) coding amino acids 141-414 was amplified by PCR using as primers

JMJD6 3' + FLAG F
(SEQ ID 26)
(5'-TGCAGCCCAAGCTTGGGCCATGGACTACAAGGACGATGACGATAAG

CACCCTAAAAGAAGG-3')
and

JMJD6 v1 3' R
(SEQ ID 27)
(5'-CTGCAGTCTAGAATCTGCTCAGGGGTGAGC-3')

and cloned into vector pcDNA3. Primer F contains a DDK sequence in frame with JMJD6 sequence.

The fragment with 804 bp (JMJD6 v2-3'/FLAG) coding amino acids 141-403 was amplified by PCR using as primers

JMJD6 3' + FLAG F
(SEQ ID 28)
(5'CTGCAGCCCAAGCTTGGGCCATGGACTACAAGGACGATGACGATAAG

CACCCTAAAAGAAGG-3')
and

JMJD6 v2 3' R
(SEQ ID 29)
(5'-CTGCAGTCTAGAACCTGGAGGAGCTGCGCTCTTTGCTG-3')

and cloned into vector pcDNA3.

Primer F contains the DDK sequence in frame with JMJD6 sequence.

All fragments were tested by digestion with restriction enzymes and sequenced. The constructs were transfected with lipofectamine (Invitrogen) in MeWo cells grown on a slide. After two days from the transfection, the cells were tested in immunofluorescence by double staining with P4E11 or anti-JMJD6 (Santa Cruz) and anti-FLAG (DDK) conjugated with Alexa 488 (Cell Signaling).

Example 1

JMJD6 Interacts with Matrix Proteins and in Particular with Collagen 1

Enzymes with lysil hydroxylase activity are present in the endoplasmic reticulum and catalyze the hydroxylation of lysine residues of collagen before the formation of the triple helix. This reaction depends on the presence of iron, 2-oxoglutarate, oxygen and ascorbate (catalysts). Since JMJD6 can show a similar enzymatic activity (hydroxylation) in the presence of the same catalysts on other molecules (various proteins involved in mRNA splicing and p53), the ability of JMJD6 to interact with collagen 1 was assayed in parallel with other extracellular matrix proteins. To this purpose, coll1, coll4, plasmatic (pFN) and cellular fibronectin (cFN) were seeded in a plate and the interaction with JMJD6v1 and v2 rec was evaluated by means of an anti-FLAG (DDK) antibody. Matrix proteins were seeded in scalar doses starting from 50 pmoles/well, the plate was incubated at 4° C. for the whole night and the following day it was reacted with JMJD6v2 rec (10 nM) at 4° C. The following day the recombinant protein that had bound collagen or other proteins was pointed out by incubation with anti-FLAG (DDK) and peroxidase-conjugated secondary antibody.

Figure 1:
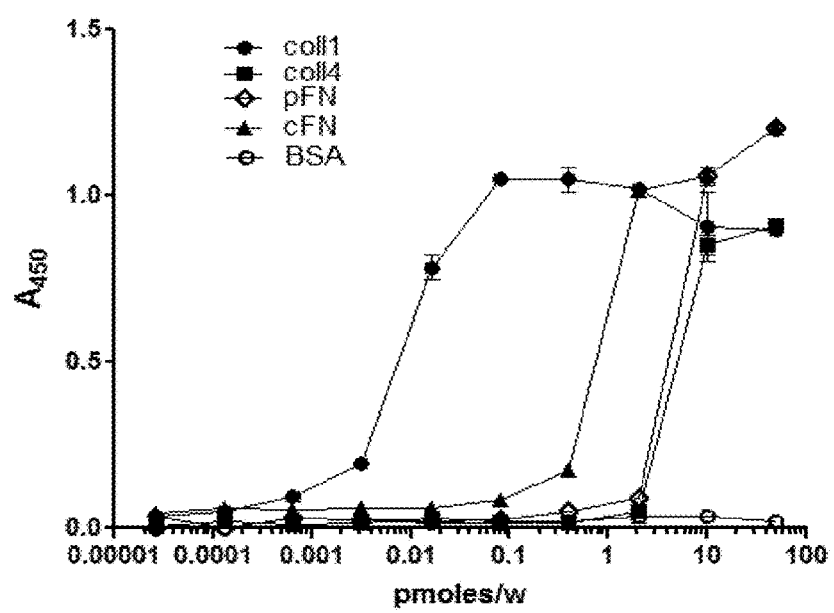
FIG. 1 shows that JMJD6 interacts with collagen 1. In frame A, the ordinates show the values of absorbance at 450 nm (A450 nm) representing the amount of complex between the assayed protein [type-1 collagen (coll1), type-4 collagen (coll4), plasmatic fibronectin (pFN), cellular fibronectin (cFN) and bovine serum albumin (BSA) acting as negative control] and one of the two human isoforms of JMJD6 (variant 1 and variant 2), which differ in the presence at C terminus of 11 additional amino acids in variant 1, in particular recombinant variant 2 (JMJD6v2 rec) carrying at C terminus a FLAG (DDK); the abscissas show the pmoles/well (pmoles/w) of each assayed protein, seeded in plates. The interaction between these proteins and JMJD6v2rec is detected by means of an anti-FLAG DDK antibody. In frame B, the ordinates show the values of absorbance a 450 nm (A450) representing the amount of complex between coll1, seeded in plates, and JMJD6v1/v2rec, the abscissas show the antibodies used for detecting this interaction; antibodies recognizing epitopes located at N terminus [αJM abn (Abnova), αJM s.c. (Santa Cruz)] or at C terminus [αJM sig (Sigma), αJM abc (Abcam), αFLAG (DDK)] of JMJD6 protein, and negative controls (contr R for rabbit antibodies and contr M for mouse antibodies).
Figure 1:
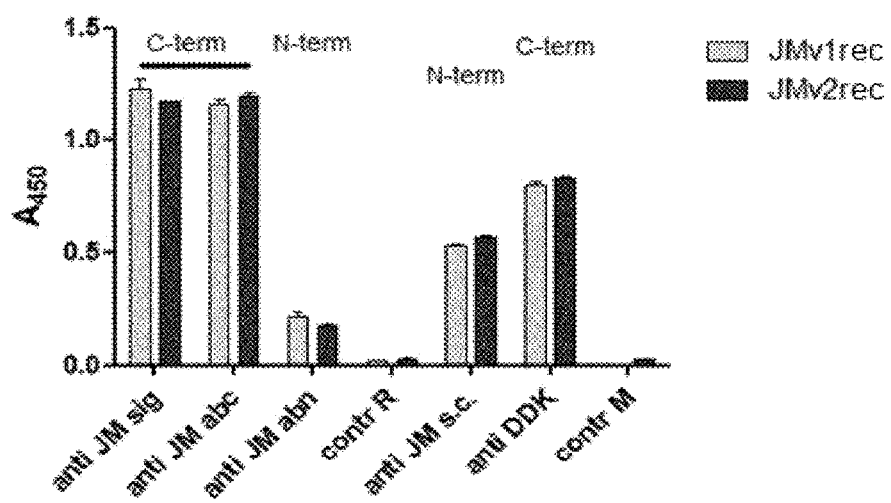

The graph in FIG. 1, frame A, shows how JMJD6 v2 can interact with all matrix proteins that were assayed, in particular with coll1 with which the binding can be detected even at very low doses (0.016 pmoles/well). At this dose no interaction with other proteins can be observed. We found that JMJD6 interacts with coll3 as well, which together with coll1 helps the formation of reticulin fibers in fibrotic tissue. We then focused on coll1 and in order to assay whether its interaction with JMJD6 could be demonstrated also with other anti-JMJD6 antibodies, a single plate collagen dose (50 pmoles) was incubated with JMJD6v1 or v2 rec (10 nM) and the interaction was detected with a panel of commercial anti-JMJD6 antibodies such as polyclonal antibodies Sigma (sig), Abcam (abc), Abnova (abn), monoclonal antibody Santa Cruz (s.c.) and anti-FLAG DDK antibody. As specificity controls purified rabbit (contr R) and mouse (contr M) IgG were used.

As shown in FIG. 1, frame B, the antibodies Sigma, Abcam and anti-DDK recognizing epitopes in the C-terminal region of the protein, have higher binding levels than antibodies directed against epitopes of the N-terminal region (Abnova and Santa Cruz). Among these, the antibody Abnova was very weakly positive.

Figure 2:
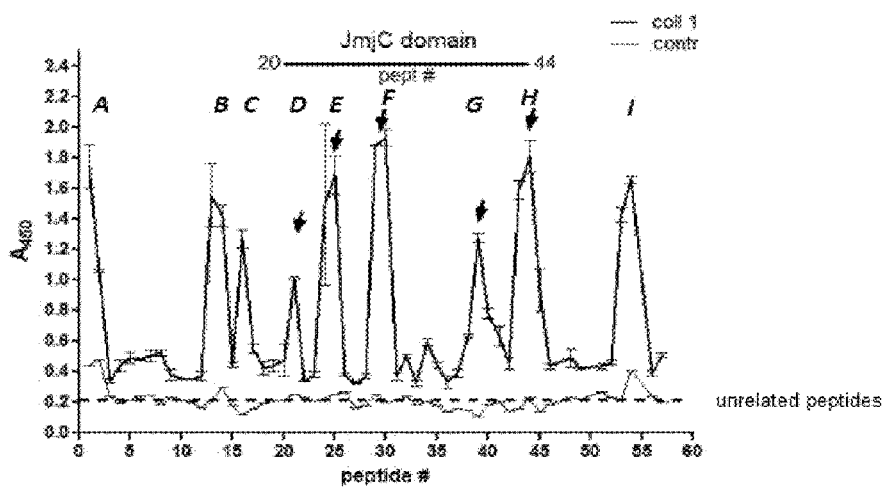
FIG. 2 shows in frame A that collagen 1 interacts in a specific manner with more JMJD6 peptides (thick continuous line). In particular, four reactivity peaks (ordinates A450 nm) are located outside JmjC domain, whereas five peaks are located inside the domain and are indicated by the arrows. No reactivity was detected with unrelated, scrambled (SCR) peptides (dashed line), whereas basic antibody reactivity without collagen is shown by the thin continuous line. Frames B and C show the ability of peptide pools corresponding to the interaction peaks with collagen and referred to with letters A, B, C, D, E, F, G, H, I (described in detail in Example 1), to modulate the interaction of the whole JMJD6v2 rec protein with collagen itself. Frame B shows a single experiment wherein in the ordinates the interaction of protein JMJD6v2 rec is expressed as A450 nm, whereas in frame C the ordinates show the average % of increase or decrease of the interaction with collagen induced by the different peptide pools, considering as 100% the binding in the presence of the pool of unrelated SCR peptides. The difference between pool I and SCR, evaluated with ANOVA test, was highly significant (***P<0.0001).
Figure 2:
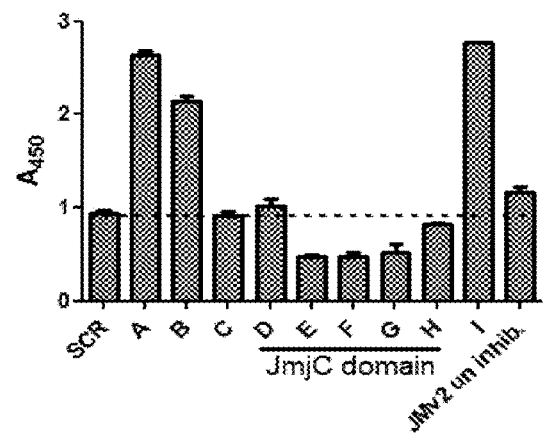
Figure 2:
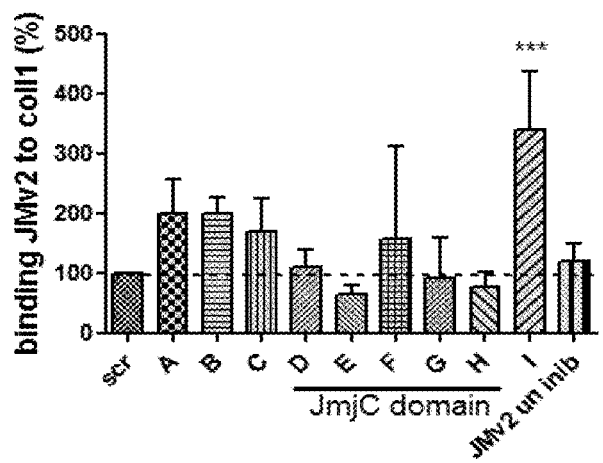

In order to understand on which part of JMJD6 protein the interaction with collagen was located, peptides with 14 amino acids, overlapping for 7 amino acids and covering the whole sequence of JMJD6 protein, were seeded in a plate and incubated with coll1 (50 pmoles/well). The binding was detected with an anti-collagen 1 antibody. As shown in FIG. 2A, more peptides are able to interact with collagen, and among these 5 peaks of interaction are located inside the catalytic site (JmjC domain). The reaction specificity is informed by the lack of interaction of coll1 with unrelated peptides, since the detected binding level is similar to the one of anti-collagen antibody in absence of collagen (contr). The identified peaks correspond to peptides 1-2 (amino acids 1-21), 13-14 (amino acids 85-105), 16-17 (amino acids 106-126), 20-21 (amino acids 134-154), 24-25 (amino acids 162-182), 29-30 (amino acids 197-217), 38-39-40-41 (amino acids 260-294), 43-44-45 (amino acids 295-322) and 53-54 (amino acids 365-385). The sequences of the peptides referred to above are listed below. The sequences that are common to each pair of group of peptides are in bold and listed on the side together with the designation of each pool of peptides then used.

| | | |
|---|---|---|
| 1 | MNHKSKKRIREAKR SEQ ID 9) | RIREAKR (SEQ ID 33) pool A |
| 2 | RIREAKRSARPELK (SEQ ID 10) | |
| 13 | WTLERLKRKYRNQK (SEQ ID 11) | RKYRNQK (SEQ ID 34) " B |
| 14 | RKYRNQKFKCGEDN (SEQ ID 12) | |
| 16 | DGYSVKMKMKYYIE (SEQ ID 13) | KMKYYIE (SEQ ID 35) " C |
| 17 | KMKYYIEYMESTRD (SEQ ID 14) | |

-continued

| | | | |
|---|---|---|---|
| 20 | DSSYGEHPKRRKLL (SEQ ID 15) | PKRRKLL (SEQ ID 36) | " D |
| 21 | PKRRKLLEDYKVPK (SEQ ID 16) | | |
| 24 | QYAGEKRRPPYRWF (SEQ ID 1) | RPPYRWF (SEQ ID 37) | " E |
| 25 | RPPYRWFVMGPPRS (SEQ ID 2) | | |
| 29 | NALVQGHKRWCLFP (SEQ ID 3) | KRWCLFP (SEQ ID 38) | " F |
| 30 | KRWCLFPTSTPREL (SEQ ID 4) | | |
| 38 | KPGETVFVPGGWWH (SEQ ID 5) | VPGGWWHVVLNLDTTIAITQN (SEQ ID 39) | |
| 39 | VPGGWWHVVLNLDT (SEQ ID 6) | | |
| 40 | VVLNLDTTIAITQN (SEQ ID 7) | | |
| 41 | TIAITQNFASSTNF (SEQ ID 8) | | pool G |
| 43 | PVVWHKTVRGRPKL (SEQ ID 17) | VRGRPKLSR KWYRI (SEQ ID 40) | |
| 44 | VRGRPKLSR KWYRI (SEQ ID 18) | | |
| 45 | SRKWYRILKQEHPE (SEQ ID 19) | | pool H |
| 53 | SEGDGTVHRRKKRR (SEQ ID 20) | HRRKKRR (SEQ ID 41) | " I |
| 54 | HRRKKRRTCSMVGN (SEQ ID 21) | | |
| Unrelated peptides | NAKVEEPRQPLVYL (SEQ ID 30)<br>GTRSVGDHPPMGH (SEQ ID 31) | " SCR | |

The existence of several points of interaction between JMJD6 and collagen led us to assume that neither the single peptides nor a single pool of peptides could be able to inhibit the binding between the two proteins. This was confirmed by experimental data (results not shown). Moreover, we observed that, if the mixtures of peptides referred to above (A, B, C, D, E, F, G, H, I and SCR) are incubated at a strong molar excess (1000×) with collagen at 37° C. for 30 mins and then seeded in a plate at 4° C. for the whole night, some of them show changes in the ability of collagen to bind recombinant JMJD6v2 protein in its whole form. As a matter of fact, as shown in FIG. 2A, peptides on extreme locations of the protein [pools A, B (N-term) and (C-term)] seem to promote the binding of JMJD6v2 with collagen with respect to those in the central zone of the protein (JmjC domain). Frame B shows the results of a single experiment, whereas the graph in frame C represents the average value of the 4 separated experiments and shows the percentage binding variation induced by each pool of peptides. We can then assume that the interaction of the N- and C-terminal regions of JMJD6 with collagen can modulate the conformation thereof, inducing e.g. the exposition of regions that can promote the interaction with the whole JMJD6 or with other matrix and cellular proteins still to be identified.

Example 2

Production of Monoclonal Antibody P4E11

Figure 3:
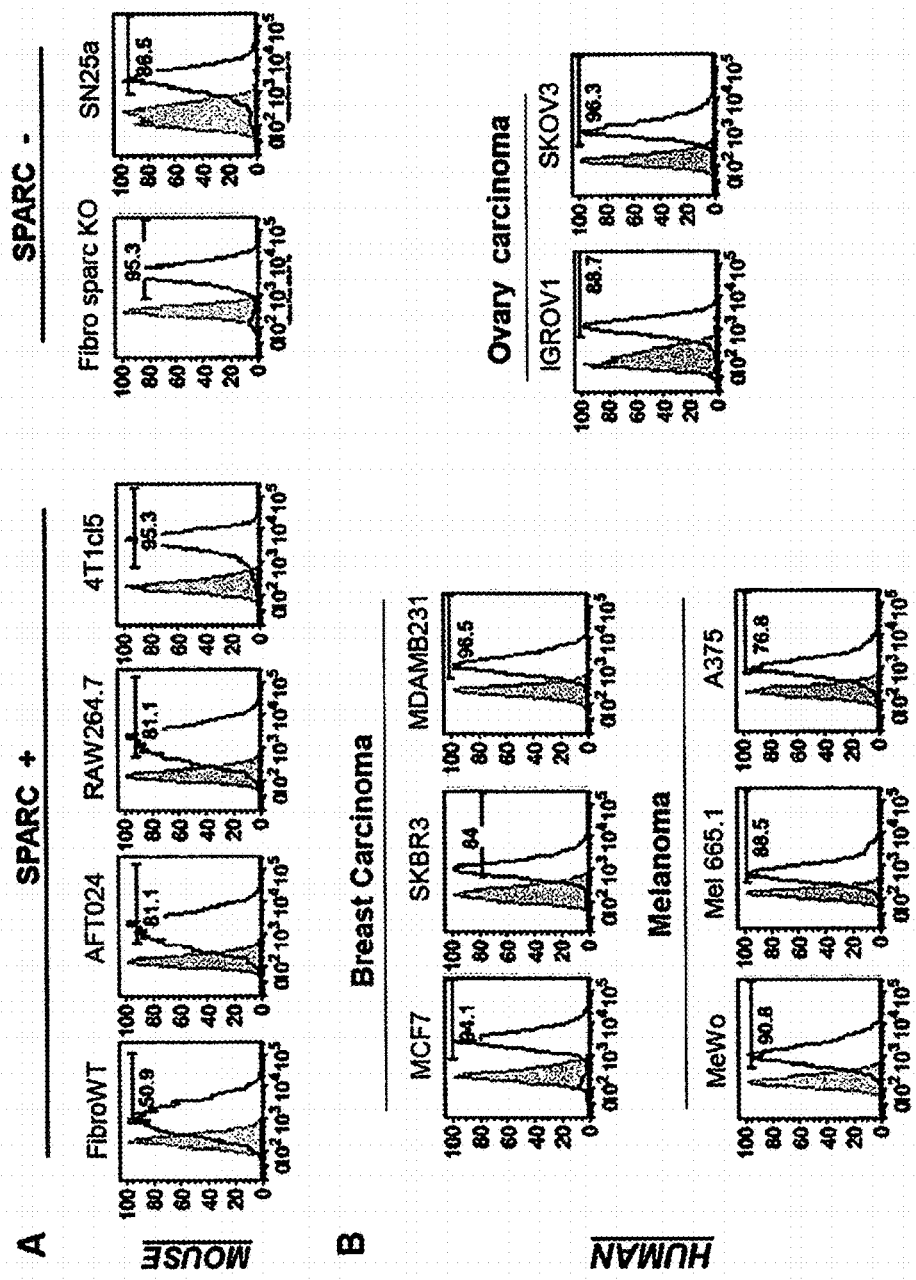
FIG. 3, frame A and B, shows the reactivity data of P4E11 antibody by means of Fluorescence-Activated Cell Sorting (FACS), performed on the following mouse (frame A) or human cell lines (frame B) and expressing matricellular SPARC protein (SPARC+) or not expressing SPARC (SPARC−): immortalized fibroblasts (FibroWT and Fibro SparcKO), stromal line AFT024, macrophage-derived line RAW264.7; lines of mouse mammary cancer 4T1cl5 and SN25a, human tumor lines of breast cancer MCF7, SKBR3 and MDAMB231, of melanoma MEWO, Mel665.1 and A375M, and of ovarian cancer IGROV1 and SKOV3. Cells were permeabilized in order to detect an intracellular expression of the protein recognized by P4E11. The negative control (grey histogram) is represented by an unrelated antibody having the same isotype (IgG2a). The ordinates show the relative number, i.e. the percentage of cells, and the abscissas show the fluorescence intensity (log.)

In order to obtain antibodies directed against components of the extracellular matrix, two Sparc$^{-/-}$ mice lacking the matricellular protein SPARC (secreted protein acidic and rich in cysteine) were immunized two times with irradiated splenocytes deriving from BALB/c mice, which are SPARC competent. After three months from the last immunization, the mice received a booster injection with splenocytes Sparc$^{+/+}$, then the splenic lymphocytes of one of them were fused with myeloma cells NS0, thus resulting in the production of hybrid cells (hybridomas) producing monoclonal antibodies (Mabs) (Kohler, G., and Milstein, G. *Continuous cultures of fused cells secreting antibody of predefined specificity. Nature* 1975; 256: 495-497,). Hybridomas were selected by culture in a selective medium (HAT-Hypoxantine-Aminopterin-Thymidine) that does not enable the growth of unfused myeloma cells, whereas lymphocytes spontaneously die after few duplications. Assuming that in mice lacking SPARC protein specific components of the extracellular matrix were immunogenic (SPARC or other SPARC-induced protein), the supernatants of the obtained hybridomas were assayed with FACs on permeabilized murine cells expressing or not expressing SPARC protein. All antibodies showed reactivity both on negative SPARC and positive SPARC cells. Among these P4E11 antibody was chosen for a further characterization. P4E11 antibody showed reactivity on normal or tumor murine cells and on tumor human cells (FIG. 3, frame A and B) and is directed against an antigen present at intracellular level.

Characterization of P4E11 Antibody

P4E11 is a IgG2a and uses VK as light chain. From the comparison with databases, the sequences of the heavy and light chains proved to belong to VH2 and VK8 germlines. The amino acid sequences of the variable regions of the heavy and light chains were sequenced as shown below (in bold CDRs, in italic frameworks and underlined the constant):

VkCk
(SEQ ID 22)
*DIQLTQSPSSLAVSAGEKVTMNCKSS*QSILYSSNHKN*YLAWYQQKPGQSP*

*KLLIY*WASTRESGVP*NRFTGSGSGTDFTLTISSVQSEDLAVYY***CHQYLSS*

*YTFGGGTKLEIK*RADAAPTVSIFPPSSEQLTSGGASVVCFLNNFYPKDIN

VKWKIDGSERQNGVLNSWTDQDSKDSTYSMSSTLTLTKDEYERH

-continued

VhCh (SEQ ID 23)
QVQLKQSGPGLVQPSQSLSITCTVSGFSLSSYGVHWVRQSPGKGLEWLGV

IWRSGNTDYNAVFMSRLSITKDDSKSQVFFKMNSLQADDTAIYYCAKNFR

YDVGSWFAYWGQGTLVTVSAAKTTAPSVYPLAPVCGDTTGSSVTLGCLVK

GYFPEPVTLTWNSGSLSSGVHTFPAVLQSDLYTLSSSVTVTSSTWPSQSI

TCNVP

VhCh (SEQ ID 32)
QVQMKQSGPGLVQPSQSLSITCTVSGFSLSSYGVHWVRQSPGKGLEWLGV

IWRSGNTDYNAVFMSRLSITKDDSKSQVFFKMNSLQADDTAIYYCAKNFR

YDVGSWFAYWGQGTLVTVSAAKTTAPSVYPLAPVCGDTTGSSVTLGCLVK

GYFPEPVTLTWNSGSLSSGVHTFPAVLQSDLYTLSSSVTVTSSTWPSQSI

TCNVP.

For uses as described below, P4E11 antibody was purified by affinity chromatography on protein A (High Trap-GE Healthcare). The purified antibody was dialyzed against saline and filtered under sterile conditions, then stored at 4° C.

Characterization of the Target Molecule

Due to its cross-reactivity on human cells, the antibody was assayed on ProtoArray (Invitrogen) comprising 9,400 human proteins. The protein present on the array were expressed and synthesized in sf9 insect cells as complete sequences, in order to preserve the native conformation and glycosylation, if any. Data were obtained by assaying P4E11 antibody at two different concentrations (0.5 µg/ml and 5.0 µg/ml). The negative control was an array in which the primary antibody was omitted and incubated only with the detection antibody, marked with fluorochrome (AlexaFluor®647-rabbit-anti-mouse IgG). The significance of the results was evaluated based on the following parameters:

Z-factor above 0.5 on the corresponding array, thus indicating the presence of a signal two times above the background signal;
Z-score (or normalized fluorescent signal) above 3.0 standard deviations on at least one array;
value of the signal used at least two times higher than the value of the corresponding signal in the negative control (which should be less than 10,000 RFU);
CI P value below 0.05;
CV (coefficient of variation) of the replicates below 50%.

The analysis (performed by Invitrogen) showed the interaction of the antibody with 16 proteins, with a different degree of significance. All the 16 proteins referred to in Table 1, FIG. 19, met the above criteria and at least one of the two antibody concentrations used. LGALS3 and LGALS8 proteins, the second and third in the list, respectively, met the criteria at both dilutions and for this reason were initially regarded as better candidates, though having a low ratio between specific P4E11 signal and negative control (14.1 and 8.8, respectively). JMJD6 and PMSD9 proteins, which had a high specific signal/negative control ratio, corresponding to 122.3 and 42.8, respectively, were then taken into consideration.

This datum was confirmed with other immunoprecipitation experiments on cell lysates and on purified recombinant JMJD6 protein (expressed and purified from human cells), in its two variants (v1 and v2). The lysate prepared as described in Materials and methods section, from non-tumor (AFT024) and tumor lines, both of murine (4T1) and human origin (MeWo, U937), were incubated with P4E11 or with an unrelated antibody of the same isotype, directly conjugated with magnetic beads (Dynabeads) epoxy-activated according to the method indicated by the manufacturer (Dynal). All beads were saturated in 0.1% PBS+ BSA and then incubated with the cell lysates for 3 hours under rotation at 4° C. After 4 washing cycles in PBS-0.1% Triton X-100, the immunoprecipitates were dissociated with 3 M NaSCN or sample buffer 1× for 5 minutes, separated from the beads by means of a magnet, recovered and then analyzed in Western Blot. P4E11 antibody immunoprecipitates from all cell lines protein bands recognized in Western Blot by a polyclonal anti-JMJD6 rabbit antibody directed against a C-terminal epitope of the molecule (αPSR, Sigma). The pattern can be reproduced and consist of a 52 kDa bands and of two high molecular weight bands of about 120 and 200 kDa. Literature data indicate a molecular weight of 52-54 kDa for JMJD6 for the formation of high molecular weight oligomers (Tibrewal et al., *Characterization of the biochemical and biophysical properties of the phosphatidylserine receptor (PS-R) gene product*. Mol Cell Biochem. 2007; 304: 119-125).

Figure 4:
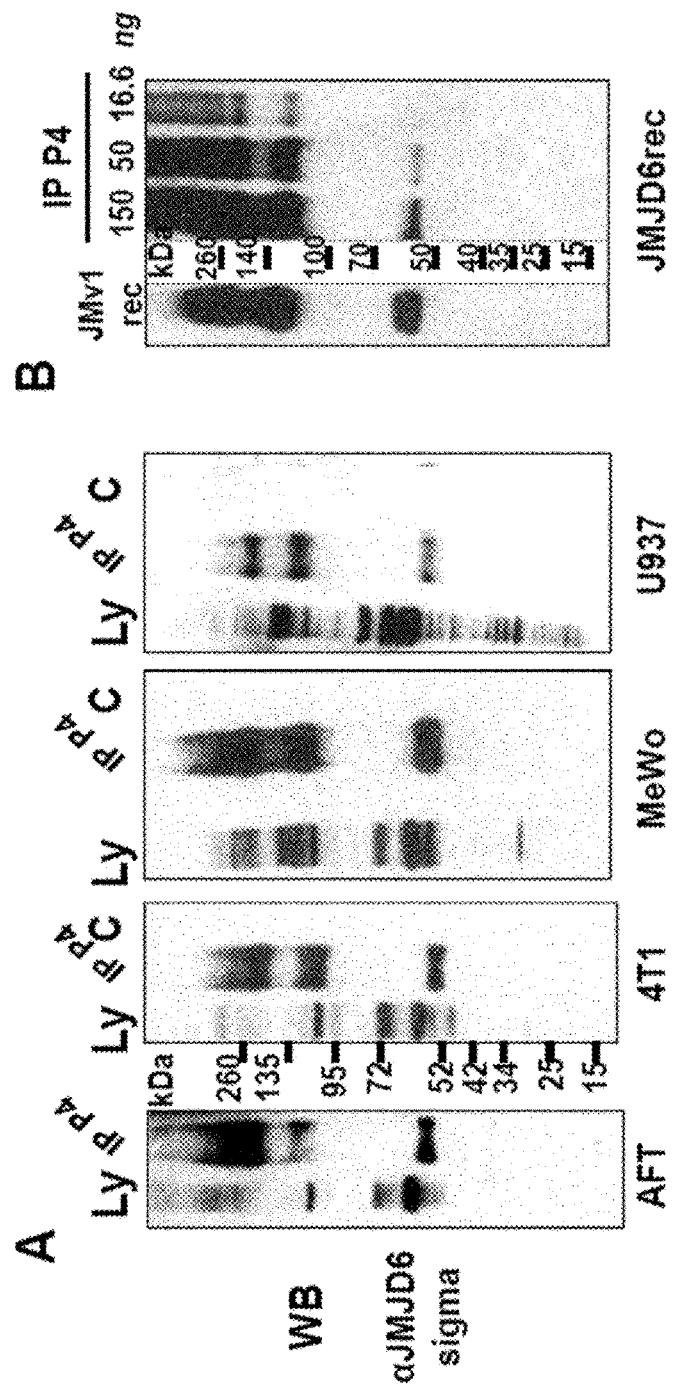
FIG. 4 shows the bands detected in Western Blot (WB) by a polyclonal anti-JMJD6 antibody in immunoprecipitates obtained with P4E11. The polyclonal anti-JMJD6 antibody (Sigma) recognizes in WB multiple bands in the total lysate (Ly) of the murine (AFT024 and 4T1cl5) or human cell lines (MeWo, U937) (FIG. 4A). Only some of these bands, with a molecular weight of about 50, 120 and 200 kDa, are enriched in the immunoprecipitate obtained by incubation of these lysates (400-600 μg of proteins) with P4E11 (IP P4). No band can be observed in the control consisting of the magnetic beads conjugated with the antibody without lysate. All the bands present in JMJD6 protein human recombinant variant 1 alone (JMv1 rec) are immunoprecipitated from P4E11 depending on the amount of recombinant protein used in IP.

As shown in FIG. 4, P4E11 antibody proved to be able to immunoprecipitate JMJD6v1 rec protein in a dose-dependent manner.

Characterization of the Epitope

A) Western Blot

Figure 5:
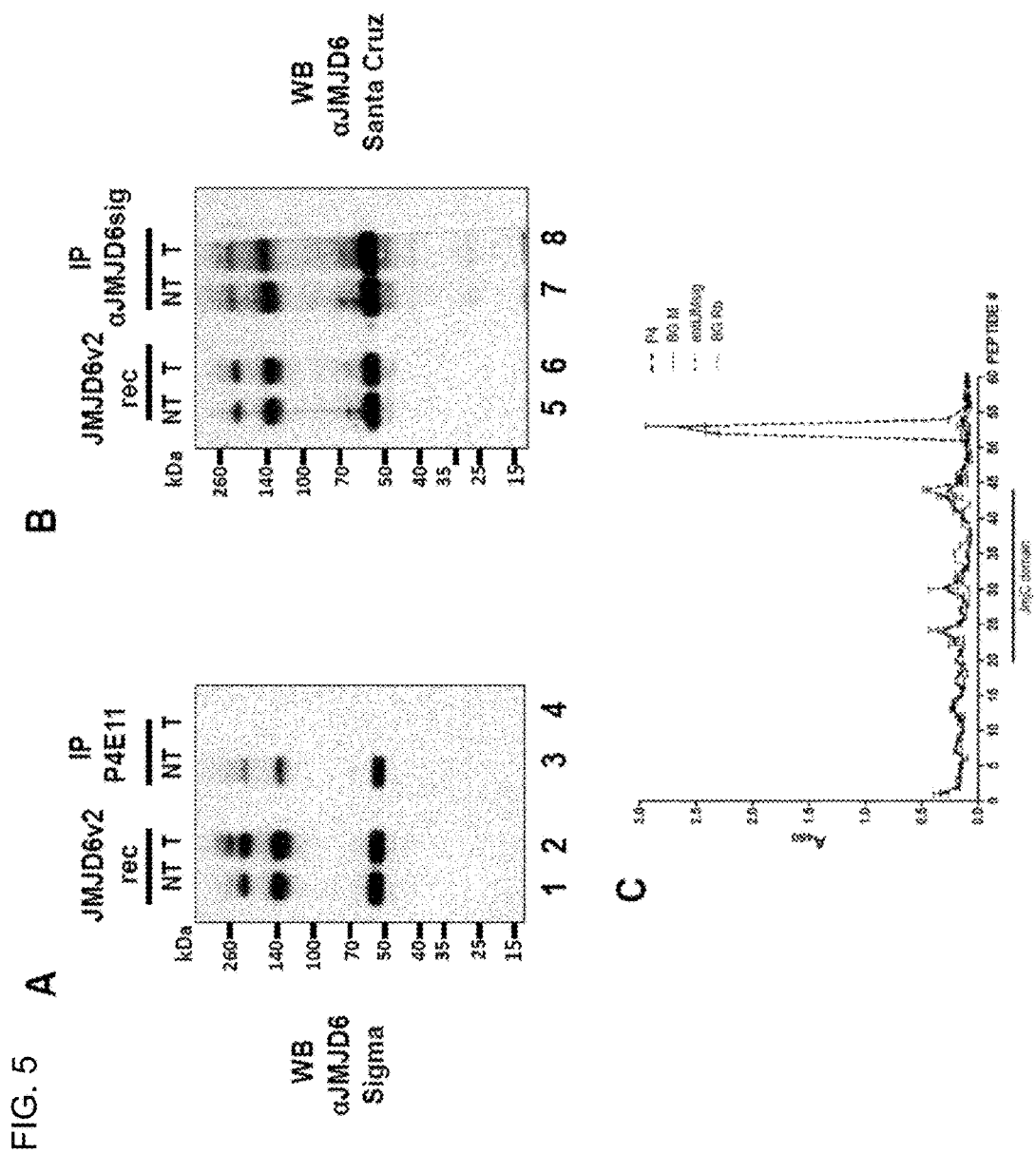
FIG. 5 shows the effect of a denaturating treatment on the recognition of JMJD6v2 rec by P4E11 in an immunoprecipitation test followed by WB with anti-JMJD6 antibodies. In frame A JMJD6v2rec, untreated (1) or subjected to denaturation treatments at 95° C. for 5 min (2), is recognized also in WB by the polyclonal anti-JMJD6 antibody (Sigma). The protein immunoprecipitated from P4E11 is detected in the immunoprecipitate before (3) and not after the denaturating treatment (4). Frame B shows that the same denaturating treatment has no effect on the epitope recognized in WB by the monoclonal anti-JMJD6 antibody (Santa Cruz) (5 and 6) and on the immunoprecipitates obtained with the polyclonal anti-JMJD6 antibody (Sigma) (7 and 8), detected with the same monoclonal anti-JMJD6 antibody (Santa Cruz). Frame C shows a graph of the reactivity of P4E11 (P4) on JMJD6 peptides, parallel to the one of commercial anti-JMJD6 antibody (Sigma) (antiJMsig), which was produced by immunization with a linear peptide corresponding to amino acids 363-381 of JMJD6. This sequence is present in peptides 52-53, where there is reactivity peak of the commercial antibody. The reactivity of secondary antibodies alone (BG M and BG Rb) is shown.

P4E11 antibody, differently from other commercial anti-JMJD6 antibodies, does not work in Western Blot and could then recognize the protein in its native form. In order to verify whether P4E11 recognized a conformation epitope, the antigen (JMJD6 var 2 rec) was heat denaturated (5 mins at 95° C.). As shown in FIG. 5, frame A, P4E11 antibody is not able to immunoprecipitate the denaturated recombinant protein since no band is recognized in WB with the commercial anti-JMJD6 antibody (Sigma) (A3 versus A4). Conversely, this antibody can recognize in WB the whole protein (A1) even after denaturation (A2) and to immunoprecipitate it (B7 and B8). As shown in FIG. 5, frame B, denaturation does not affect the recognition of the protein by another commercial anti-JMJD6 antibody (αPSR, Santa Cruz, N-term epitope) (B5 and B6) even after immunoprecipitation (B7 and 8). These data suggest that, differently from the other two anti-JMJD6 antibodies, P4E11 recognizes on this protein an epitope that is sensitive to heat denaturation. The conformational nature of the epitope was confirmed by the lack of reactivity of P4E11 antibody on sequential, partially overlapping JMJD6 peptides seeded in a plate and assayed as described in Materials and methods (FIG. 5C). On the contrary, the polyclonal anti-JMJD6 antibody (Sigma), obtained by immunization against a linear peptide, correctly recognizes the immunizing sequence present in peptides 52-53. In order to locate the epitope recognized by P4E11 on JMJD6 protein, melanoma cells MeWo were transfected with truncated constructs of the two isoforms of the protein (var2 and var1) which differ on C terminus in a sequence of 11 amino acids (403 versus 414aa respectively). These constructs, designated 5'/FLAG (same sequence for both isoforms), var1-3'/FLAG and var2-3'/FLAG, described in Materials and methods and whose structure is shown in FIG. 6, frame A, contained JmjC domain but were deprived on the sequences downstream or upstream from the domain itself. In these cDNAs a FLAG (DDK) sequence was located downstream (5'/FLAG) or upstream from JmjC domain (v1-3'/FLAG, v2-3'/FLAG). The cells, sown onto a slide, were transfected with the various constructs and after 48 h from transfection were analyzed in immunofluorescence by double staining with anti-FLAG (DDK) conjugated with Alexa 488 (Cell Signaling) and P4E11 or anti-JMJD6 (Santa Cruz) or anti-JMJD6 (Sigma). As shown in FIG. 6, frame B, the overexpression of the truncated sequence of 5'/FLAG protein is recognized by an anti-FLAG (DDK) antibody and by αJMJD6 antibody (Santa Cruz) directed against an epitope located in the region at N terminus (amino acids 1-300). On the contrary, the overexpression of the truncated forms of JMJD6 (v1 and v2 3'/FLAG) was detected with αJMJD6 antibody (Sigma) recognizing the C-terminal region (results not shown). However, we have not detected an increase of reactivity of P4E11 in FLAG positive cells transfected with 5'/FLAG or with the other two constructs and this demonstrates that the whole protein sequence is required for preserving the conformation recognized by our antibody. Therefore, this confirms that the epitope is not preserved in absence of the complete protein since it is strictly related to the conformation of the protein itself, as also shown by data in FIG. 5.

The conformation of the molecule proved to be important also in an immunoenzymatic test (ELISA) based on the simultaneous recognition on the protein of two epitopes by two different antibodies. FIG. 7 represents the two possible combinations in which P4E11 was used together with anti-JMJD6 antibody Sigma. As shown in FIG. 7, frame A and frame C column 1, in Example A, in which P4E11 adheres to the plate, the interaction with the recombinant protein is detected by the commercial αJMJD6 antibody (Sigma). On the contrary, as shown in FIG. 7, frame B and frame C column 2, if αJMJD6 antibody (Sigma) is seeded in a plate and therefore the interaction with P4E11 occurs as a secondary event, the recognition does not take place. As shown in FIG. 7, frame C columns 3 and 4, in the latter condition the recombinant protein is indeed recognized by other antibodies directed against JMJD6, which recognize an epitope both at N term (αJMJD6 Santa Cruz (s.c.) and at C term (αFLAG DDK).

Therefore, since the epitope is available on the protein in its native conformation and as such is recognized by the antibody of the invention, this recognizes the protein if it interacts first with the protein itself (C-1), but is no longer available if the protein has interacted before with another antibody (C-2).

From all these experiments it can be assumed that P4E11 recognizes JMJD6 in a specific conformation that can be modulated by the interaction of the protein with other molecules, whether these are antibodies as shown above or other intra- and/or extracellular proteins.

B) Epitope Mapping

The epitope mapping of P4E11 confirmed its conformational nature. The epitope recognized by P4E11 was identified through the sequencing of aa stretches protected from proteases digestions because of P4E11-JMJD6 interaction (FIG. 7'). Three of such stretches are located in the JMJD6 N-term region, and their sequences correspond to aa 14-19 (RSARPE), included in peptides 1-2 (pool A), to aa 78-84 (GWSAQEK) included in peptides 11-12, and to aa 114-125 (MKYYIEYMESTR) included in peptides 16-17 (Pool C). Other 3 sequences are located in the JmjC domain and correspond to aa 155-167 (FFTDDLFQYAGEK) included in peptides 22-23, to aa 182-216 (SGTGIHIDPLGT-SAWNALVKGKKRWCLFPTSTPRE) in peptides 26-27-28-29-30 (Pool F), and to aa 225-252 (AITWFNVIYPR) included in peptides 33-34-35. Sequences reported in bold correspond to SEQ ID 35 (MKYYIE) and SEQ ID 38 (KRWCLFP), respectively, confirming that at least two sequences of at least 5 aa each are involved both in collagen and P4E11 interaction. To be noted that an additional sequence (RSARPE) included in SEQ ID 10 and corresponding to the JMJD6 peptide #2 (Pool A) was found to share these properties. All together these results demonstrate that the interaction of P4E11 with JMJD6v2rec interferes with the binding of JMJD6v2rec to coll1 in three distinct points.

Example 3

Analysis of the Localization of JMJD6 Protein

As shown in FIG. 8, the analysis by immunofluorescence with a confocal microscope on non-permeabilized cells demonstrates that P4E11 antibody (highlighted with a secondary antibody marked with fluorochrome) identifies in the assayed lines some cells expressed in the protein membrane, whereas in permeabilized cells the antigen is expressed in all the cells and is located both in the cytoplasm and in the nucleus in all the examined lines.

Localization of JMJD6 in the Extracellular Matrix

P4E11 antibody and the two commercial antibodies (αJMJD6 Sigma and αJMJD6 Santa Cruz) directed against different regions of JMJD6 proteins (against C- and N-term epitopes, respectively) were used in immunohistochemical experiments on a panel of human mammary tumors (22 cases) for analyzing the presence and distribution of the protein. FIG. 9 shows 3 exemplary cases documenting the staining obtained with P4E11 and with the other two anti-JMJD6 antibodies. All the three antibodies used have detected the presence of the protein in 100% of the cases. On the contrary, protein distribution was not overlapping in the three antibodies from a percentage point of view. All the three antibodies recognize the protein at nuclear and cytoplasmic level. A specific extra-tumor staining at stroma level was further detected.

As shown in FIG. 10, P4E11 antibody marks the protein with intracellular cytoplasmic localization in about 72% of the cases, whereas in 22% of the cases it marks the protein with a combined nuclear/cytoplasmic pattern. The stroma is stained in most of the cases (86%). In only one case the expression in the membrane associated with cytoplasmic marking was observed. The relative low frequency of the presence of the protein in the membrane is in accordance with what was detected in the cell lines, wherein only a fraction of the total population was positive (see FIG. 8). The polyclonal anti-JMJD6 antibody by Sigma has a very similar reactivity to the one of P4E11, with marking percentages of 78% (only cytoplasm), 14% (nuclei/cytoplasm) and 93% (stroma).

The staining of the monoclonal anti-JMJD6 antibody by Santa Cruz, on the contrary, is mainly marked at nuclear/cytoplasmic level (43%), in 22% of the cases only the nuclei are marked whereas cytoplasmic-only marking is more limited (30%). The stroma is positive in 78% of the cases.

These results demonstrate for the first time that JMJD6 protein can also be localized at extracellular level.

Moreover, the results demonstrate that antibodies directed against different regions of the molecule allow to highlight a different endocellular distribution of the protein; the percentage of cases in which the cytoplasmic or nuclear form is recognized varies among the antibodies, though being similar between P4E11 and anti-JMJD6 Sigma. This can also be affected, beyond by the different epitopes recognized, by the preferential recognition of the monomer form at about 50 kDa rather than of high molecular weight oligomers, or by post-translational modifications of the protein, such as e.g. phosphorylation.

JMJD6 is Releases In-Vitro and can be found in the Supernatant of Cell Lines.

The presence of JMJD6 in the stroma suggested that the protein could be released by the cells. Therefore, the supernatant of various tumor lines was assayed in order to verify the presence of released forms of JMJD6.

In detail, the cells at 90% confluence, after 4 washing cycles with a phosphate buffer solution (PBS) and a washing cycle with a medium without fetal bovine serum, were incubated with the same medium without FBS for 24 hours. The recovered supernatant was centrifuged for 10 minutes at 1,300 rpm and then 20 minutes at 2,600 rpm so as to eliminate cells and debris, if any, and to obtain a clarified supernatant. The latter was then concentrated 40-50× with microconcentrators (cut off 3000 daltons, Agilent), dosed for the amount of protein with Bradford (Biorad), then analyzed in Western Blot with the two commercial antibodies by Sigma and Santa Cruz. In parallel, the cells were lysated and also subjected to Western Blot with the same two antibodies. The results are shown in FIG. 11. All the lines of carcinoma (mammary and ovarian cancer) and the melanomas release the protein in the supernatant, as well as the lymphoblastoid line Jurkat, which grows in suspension.

Moreover, anti-JMJD6 antibody by Santa Cruz recognized above all the monomer form of about 50 kDa, see FIG. 11, frame A, anti-JMJD6 antibody by Sigma preferentially identifies high molecular weight forms, see FIG. 11, frame B.

P4E11 antibody is able to immunoprecipitate from the culture supernatant of MeWo cells the high molecular weight forms recognized by the polyclonal anti-JMJD6 antibody by Sigma. The polyclonal antibody by Sigma immunoprecipitates in its turn JMJD6 from the supernatant, but differently from P4E11 above all the monomer protein of 50 kDa is immunoprecipitated, identified in Western Blot by anti-JMJD6 Santa Cruz, see FIG. 12, frame A. The protein detected in the culture supernatant of MeWo cells is a soluble protein, which is only partially sedimentable after high-speed ultracentrifugation, see FIG. 12, frame B. As a matter of fact, in order to verify whether JMJD6 released in the supernatants was associated with microvesicles/exosomes, the unconcentrated supernatant is further centrifuged for 30 mins at 10,000×g (S) and then ultracentrifuged for 2 hours at 100,000×g (S1). The supernatant thus obtained was then concentrated as described above and the pellet is resuspended directly in the sample preparation buffer (1×) for Western Blot analysis. The comparison using the same volumes suggests that the majority of JMJD6 is present in soluble form in S1, whereas a small aliquot of the 50 kDa form can be detected with anti-JMJD6 Santa Cruz also in the pellet containing the particulate fraction, which is positive in WB for exosome marker CD63. The results thus obtained demonstrate that JMJD6 is released from the cells mainly in soluble form and it is partially present also in a particulate form associated with exosomes. Both forms could be associated with the stroma and interact with components of the extracellular matrix.

Example 4

Biologic Activity of Inhibitors of JMJD6
1. Fibrosis

The analysis of the expression of JMJD6 in a number of cryostatic sections of human tissues under repair/regeneration highlighted reactivity at stroma level (results not shown). This type of reactivity at stroma level had already been observed in the panel of mammary tumors whose staining (FIG. 9) and analysis (FIG. 10) were shown.

The expression of the target protein in stromal and inflammatory cells and in the stroma itself, suggested a potential profibrotic activity of JMJD6.

In order to verify whether the interaction of JMJD6 with the antibody resulted in the inhibition of fibrotic phenomena, P4E11 antibody was assayed using two different experimental models for fibrosis induction.

Pulmonary Fibrosis

Pulmonary fibrosis was induced in BALB/c mice by administration of bleomycin as described in Sangaletti et al., (SPARC oppositely regulates inflammation and fibrosis in bleomycin induced lung damage. Am J Pathol 2011. 179: 3000-3010). In short, 4 groups of mice (5 animals per group) were created and after anesthesia with ketamine (100 mg/kg) and xylazine (5 mg/kg) were administered bleomycin (0.15 U/mouse) in saline, bleomycin associated with the antibody in saline, antibody in saline or saline alone. The antibody was administered at a dose of 250 µg/mouse, twice a week for two weeks by means of intraperitoneal inoculum. The treatment with bleomycin (single dose) was administered by means of intratracheal instillation. After 16 days mice were sacrificed and lungs removed to undergo histological analysis. Three samples of mice, untreated or treated with P4E11 antibody alone, were examined, whereas all available samples of mice treated with bleomycin, in association or not with the antibody, were analyzed. In the group of mice treated with bleomycin alone, an animal had died before the removal.

In detail, the lungs were fixed in situ, after sacrificing the animal, by means of intratracheal inoculum of buffered formalin, removed and left in formalin for 24 hours.

FIG. 13 shows histological lung sections of 4 µm stained with hematoxylin and eosin. As can be seen, mice treated with bleomycin and saline show interstitial parenchymal densifications, increase of interstitial cellularity by recruitment of polymorphonucleated granulocytes and fibroblast and pneumocyte proliferation, and signs of exudative alveolitis. These effects are effectively contrasted by the antibody, as can be inferred from the samples obtained by mice in which bleomycin administration was associated with antibody treatment, which show a limited fibrosis and a partially intact structure of the pulmonary parenchyma with respect to those treated with saline.

Pulmonary fibrosis was evaluated based on a semi-quantitative method (as described in Sangaletti et al., Am J Pathol 2011) which takes into account a series of variables such as the thickening of the alveolar wall, the entity of the interstitial inflammatory infiltrate, of fibroblast proliferation, of the proliferation of epithelial cells, extracellular collagen deposition, amount of intracellular collagen, the global entity of parenchymal damage.

The global evaluation of the experiment, depicted in FIG. 14, shows that in mice treated with bleomycin alone (4/5 survived animals) the parenchymal damage varies from 0 to 2 (median value 2) and the degree of fibrosis is of 0 to 2 with a median value of 1, whereas the treatment with P4E11 antibody is able to reduce both the levels of parenchymal damage (median value 1, range 0-3) and the degree of fibrosis (median value 0, range 0-2). Similar results were obtained in a second experiment.

Medullary Fibrosis (Myelofibrosis)

Medullary fibrosis was induced in BALB/c mice by means of treatment with recombinant murine thrombopoietin (TPO, PeproTech) as described in Tripodo et al., (*Stromal SPARC contributes to fibrotic detrimental changes associated with myeloproliferation whereas its deficiency favors myeloid cell expansion. Blood* 2012; 120: 3541-3554). As for the treatment with bleomycin, 4 groups of mice (5 animals per group) that received TPO in saline, TPO associated with the antibody in saline, antibody in saline or saline alone, respectively. The inoculum was performed intraperitoneally at a dose of 500 mg/kg and repeated every day for 10 consecutive days. After sacrificing the animals, femora, tibiae and spleen were collected, fixed in formalin immediately after removal and included in paraffin to undergo histopathological analysis. The histopathological analysis was performed on 4 μm sections stained with hematoxylin and eosin and Gomori staining. Medullary fibrosis was evaluated in a semi-quantitative manner, assigning a value from 0 (normal) to 3 (diffused and thick increase of reticulin with a large amount of intersections of big collagen fibers associated with osteosclerosis) according to what is described in *Tripodo et al.*, (Blood 2012).

The results of the histological analysis of the bone tissue of the femoral medullary parenchyma are shown in FIG. 15, in which it can be seen that in all mice treated with TPO there occurs a deposition of thick reticulin fibers and of collagen. Fibrosis in mice treated with TPO, evaluated in a semi-quantitative manner (4 levels, 0-3), has a median level of 3 (range 1-3). In mice treated with TPO in association with P4E11 antibody, the same myeloproliferation can be observed but fibrosis is weaker and characterized by a lower deposition of reticulin and less thick collagen fibers. The degree of fibrosis in mice treated with TPO and P4E11 is of 1 to 2, with a median value of 2.

Fibrosis of Tumor Tissue

The effect of JMJD6 blocking on intratumor fibrosis was evaluated in the murine model of mammary cancer 4T1c15. At the same time, the modulation of the growth of the primary tumor and the inhibition of the metastatic process were evaluated. Four experiments were conducted, in which two groups of BALB/c mice, each group consisting of five-seven animals, were inoculated with $7 \times 10^3$ cells under skin in the mammary fat, and the primary tumor growth was monitored for four weeks. In the first group, mice were treated with P4E11 at a dose of 250 μg/inoculum, intraperitoneally, starting from the day before tumor inoculum, twice a week for four weeks. In the second group, the control group, mice were inoculated with saline. In two experiments another group (4-6 animals) was added as control, treated with an unrelated antibody of the same isotype as P4E11 (IgG2a), with the same dosage regimen used for P4E11. At the end of the treatment, the animals were sacrificed after being anesthetized, the primary tumor was size evaluated and removed, lungs were used for the clonogenic test (Sangaletti et al., *Macrophage-derived SPARC bridges tumor cell-extracellular matrix interactions toward metastasis. Cancer Research* 2008; 68: 9050-9059). In short, after fragmentation and enzymatic digestion with collagenase IV/elastase for 140 mins at 4° C., the suspension was filtered, centrifuged and the cellular component was sown at three dilutions (1:2, 1:10, 1:100) in Petri plates (100 mm) in DMEM with thioguanine (10 ug/ml). The number of colonies was evaluated after 15 days of growth after fixation with methanol and staining with methylene blue.

As shown in FIG. 16, four independent experiments have demonstrated that the treatment with P4E11 antibody is able to significantly reduce the metastatic process. The same result was not observed with an unrelated antibody of the same isotype or without the antibody.

The histological and histochemical analysis allowed to detect a change of the extracellular matrix surrounding the cells of the primary tumor in mice treated with the antibody.

In particular, as shown in FIG. 17, Gomori staining shows a lower deposition of reticulin fibers in tumors of treated mice with respect to untreated mice. A lower collagen deposition and matrix complexity is highlighted with trichrome staining, too (results not shown).

In order to confirm these data also in tumors of human origin, xenotransplants of cells of mammary cancer MDA MB231 and of ovarian cancer IGROV1 were analyzed. In detail, in the case of mammary cancer MDA MB231, $5 \times 10^6$ cells were inoculated under skin into immunodeficient mice (SCID), and the growth was monitored for 3-4 weeks. The treatment groups (5 animals per group) included animals inoculated with P4E11 (same therapeutic regimen as above) and control animals inoculated with saline. At the end primary tumors were removed and fixed in formalin. In the case of ovarian cancer IGROV1, $5 \times 10^6$ cells were inoculated intraperitoneally into immunodeficient mice (NUDE), and the growth was monitored for about 3 weeks. The treatment groups (5 animals per group) included animals inoculated with P4E11 (same therapeutic regimen as above) and control animals inoculated with saline. After about 2 weeks, in the presence of weight increase and abdomen swelling probably due to tumor growth with formation of ascitic liquid, the animals were sacrificed. The inoculum of MDA MB231 cells led to the formation of primary tumors under skin, without evidence of macroscopic pulmonary metastasis both in animals treated with the antibody and in the control group. On the contrary, IGROV1 cells grew as multicellular aggregates freely moving in the abdomen or associated with the peritoneal membrane. The histological analysis (Gomori and trichrome staining) was conducted on solid tumors MDA MB231 and on peritoneal fragments with adhering aggregates of IGROV1 cells. In both cases the analysis of the tumor fragments showed a change of the stromal component, with a reduction of collagen and reticulin fibers.

The results listed above confirm that JMJD6 blocking has an antifibrotic effect in normal or tumor tissues.

P4E11 modulation of fibrosis inside the tumor is a relevant object of the antibody activity, since the presence of a strong fibrotic component, produced both by microenvironment cells and by tumor cells themselves subjected to epithelial mesenchymal transition, can affect the response to therapy. As a matter of fact, the content and structural organization of collagens, by increasing the density of the matrix and the pressure of the interstitial fluid, can negatively affect the accessibility of drugs to tumor (Egebla et al., *Dynamic interplay between collagen scaffold and tumor evolution. Curr Opin Cell Biol* 2010. 22: 697-706)

Example 5

The Biologic Activity of Inhibitors of JMJD6 is Realized through the Block of the Interaction of JMJD6 with Collagen The ability of the antibody to reduce fibrosis, both induced in normal tissues (lung, bone marrow) or located inside the tumor tissue, suggests that it can interfere with the interaction of JMJD6 with extracellular matrix proteins.

In order to evaluate how P4E11 antibody can interact with JMJD6 after it bound to collagen, the Elisa assay shown in FIG. 1, frame B, was repeated using anti-JMJD6 antibody by Sigma as a positive control of interaction. This assay shows that P4E11 antibody is absolutely not able to detect JMJD6 after interaction thereof with collagen, so that it can be assumed that P4E11 and collagen are mutually exclusive with respect to the interaction JMJD6, and as a result that P4E11 recognizes an epitope on JMJD6 corresponding to one of sites of interaction with collagen 1, or that after interaction with the antibody the change of JMJD6 conformation is such as not to enable the interaction with collagen itself.

In order to confirm this assumption, an ELISA assay was prepared, in which first the interaction between P4E11 sown in a plate and recombinant JMJD6 protein occurs, then col11 at three different doses is added (50, 5 and 0.5 pmoles/well). It was then evaluated whether after the addition of collagen the presence of recombinant JMJD6 could be detected using anti-JMJD6 antibody Sigma as well as the presence of collagen using an anti-collagen antibody.

As shown in FIG. 18, frame B, left side, in three separate experiments it was observed that anti-col11 antibody cannot detect the presence of collagen if JMJD6 has already interacted with P4E11, unless collagen is present in a molar excess (50 pmoles col11 versus 2 pmoles JMJD6v2 rec), in which case a slight binding can be observed (−●−). The same frame also shows how the recombinant protein bound to P4E11 is however correctly detected by anti-JMJD6 antibody sigma (−■−), even though in the presence of the highest collagen dose a reduction of the binding can be observed with respect to the sample in which col11 is not present (−▲−). This indicates that, despite the presence of collagen, JMJD6 protein is still bound to P4E11.

The same test was conducted with anti-JMJD6 antibody Sigma in a plate (FIG. 18, frame B, right side). In this case, the anti-collagen antibody emits a positive signal (−●−), thus demonstrating that recombinant JMJD6 protein, which was bound to the antibody and detected with anti-FLAG (DDK), simultaneously interacts also with collagen (−■−), and at similar levels with respect to the sample in which col11 is not present (−▲−).

These results confirm that P4E11 interferes with the interaction between collagen and JMJD6. We assume that this property is responsible for the inhibition of fibrotic processes in animals treated with P4E11.

The invention claimed is:

1. A monoclonal antibody or a fragment thereof,
   wherein the monoclonal antibody or a fragment thereof binds to JMJD6,
   wherein the monoclonal antibody or a fragment thereof comprises a light chain variable region and a heavy chain variable region,
   wherein the light chain variable region comprises the following CDRs: QSILYSSNHKN (SEQ ID NO:42), WASTRESGVP (SEQ ID NO:43), and HQYLSS (SEQ ID NO:44); and
   wherein the heavy chain variable region comprises the following CDRs: GFSLSSYG (SEQ ID NO:45), IWRSGNT (SEQ ID NO:46), and AKNFRYDVG-SWFAY (SEQ ID NO:47).

2. The monoclonal antibody or a fragment thereof according to claim 1, wherein the variable region of the light chain (VkCk) or a fragment thereof comprises the following sequence:

(SEQ ID NO: 22)
NIMMTQSPSSLAVSAGEKVTMNCKSSQSILYSSNHKNYLAWYQQKPGQSP

KLLIYWASTRESGVPNRFTGSGSGTDFTLTISSVQSEDLAVYYCHQYLSS

YTFGGGTKLEIKRADAAPTVSIFPPSSEQLTSGGASVVCFLNNFYPKDIN

VKWKIDGSERQNGVLNSWTDQDSKDSTYSMSSTLTLTKDEYERH and wherein the variable region of the heavy chain (VkCh) comprises one of the following sequences:

(SEQ ID NO: 23)
QVQLKQSGPGLVQPSQSLSITCTVSGFSLSSYGVHWVRQSPGKGLEWLGV

IWRSGNTDYNAVFMSRLSITKDDSKSQVFFKMNSLQADDTAIYYCAKNFR

YDVGSWFAYWGQGTLVTVSAAKTTAPSVYPLAPVCGDTTGSSVTLGCLVK

GYFPEPVTLTWNSGSLSSGVHTFPAVLQSDLYTLSSSVTVTSSTWPSQSI

TCNVP
or (SEQ ID NO: 32)
QVQMKQSGPGLVQPSQSLSITCTVSGFSLSSYGVHWVRQSPGKGLEWLGV

IWRSGNTDYNAVFMSRLSITKDDSKSQVFFKMNSLQADDTAIYYCAKNFR

YDVGSWFAYWGQGTLVTVSAAKTTAPSVYPLAPVCGDTTGSSVTLGCLVK

GYFPEPVTLTWNSGSLSSGVHTFPAVLQSDLYTLSSSVTVTSSTWPSQSI

TCNVP.

3. The monoclonal antibody or a gragment thereof according to claim 1, produced from the hybridoma deposited with the Autorita Internazionale di Deposito (AID) Centro di Biotecnologie Avanzate (CBA)—Interlab Cell Line Collection (ICLC) of Genoa (Italy), access number PD 15001.

4. A method of treating fibrosis, treating a tumor, or treating tumor metastases in a subject, the method comprising administering a pharmaceutically effective amount of the monoclonal antibody or a fragment thereof of claim 1 to the subject.

5. A pharmaceutical composition comprising a monoclonal antibody or a fragment thereof according to claim 1 and at least one pharmaceutically acceptable carrier and/or excipient.

6. The method according to claim 4, the method further comprising administering at least one chemotherapeutic drug.

7. The method according to claim 4, wherein said chemotherapeutic drug is selected from bleomycin, fludarabine and methotrexate.

8. A hybridoma deposited with the Autorità Internazionale di Deposito (AID) Centro di Biotecnologie Avanzate (CBA)—Interlab Cell Line Collection (ICLC) of Genoa (Italy), access number PD 15001.

9. The method of claim 4, wherein the fibrosis comprises pulmonary, peritoneal, medullary, or tumor tissue fibrosis.

10. The method of claim 4, wherein the tumor metastases comprise metastases of mammary or ovarian cancer.

11. The method of claim 4, wherein the method further comprises treating the subject with radiotherapy and/or chemotherapy.

* * * * *

SEQUENCE LISTING

```
<160> NUMBER OF SEQ ID NOS: 47

<210> SEQ ID NO 1
<211> LENGTH: 14
<212> TYPE: PRT
<213> ORGANISM: Homo sapiens

<400> SEQUENCE: 1

Gln Tyr Ala Gly Glu Lys Arg Arg Pro Pro Tyr Arg Trp Phe
1               5                   10

<210> SEQ ID NO 2
<211> LENGTH: 14
<212> TYPE: PRT
<213> ORGANISM: Homo sapiens

<400> SEQUENCE: 2

Arg Pro Pro Tyr Arg Trp Phe Val Met Gly Pro Pro Arg Ser
1               5                   10

<210> SEQ ID NO 3
<211> LENGTH: 14
<212> TYPE: PRT
<213> ORGANISM: Homo sapiens

<400> SEQUENCE: 3

Asn Ala Leu Val Gln Gly His Lys Arg Trp Cys Leu Phe Pro
1               5                   10

<210> SEQ ID NO 4
<211> LENGTH: 14
<212> TYPE: PRT
<213> ORGANISM: Homo sapiens

<400> SEQUENCE: 4

Lys Arg Trp Cys Leu Phe Pro Thr Ser Thr Pro Arg Glu Leu
1               5                   10

<210> SEQ ID NO 5
<211> LENGTH: 14
<212> TYPE: PRT
<213> ORGANISM: Homo sapiens
```

<400> SEQUENCE: 5

Lys Pro Gly Glu Thr Val Phe Val Pro Gly Gly Trp Trp His
1               5                   10

<210> SEQ ID NO 6
<211> LENGTH: 14
<212> TYPE: PRT
<213> ORGANISM: Homo sapiens

<400> SEQUENCE: 6

Val Pro Gly Gly Trp Trp His Val Val Leu Asn Leu Asp Thr
1               5                   10

<210> SEQ ID NO 7
<211> LENGTH: 14
<212> TYPE: PRT
<213> ORGANISM: Homo sapiens

<400> SEQUENCE: 7

Val Val Leu Asn Leu Asp Thr Thr Ile Ala Ile Thr Gln Asn
1               5                   10

<210> SEQ ID NO 8
<211> LENGTH: 14
<212> TYPE: PRT
<213> ORGANISM: Homo sapiens

<400> SEQUENCE: 8

Thr Ile Ala Ile Thr Gln Asn Phe Ala Ser Ser Thr Asn Phe
1               5                   10

<210> SEQ ID NO 9
<211> LENGTH: 14
<212> TYPE: PRT
<213> ORGANISM: Homo sapiens

<400> SEQUENCE: 9

Met Asn His Lys Ser Lys Lys Arg Ile Arg Glu Ala Lys Arg
1               5                   10

<210> SEQ ID NO 10
<211> LENGTH: 14
<212> TYPE: PRT
<213> ORGANISM: Homo sapiens

<400> SEQUENCE: 10

Arg Ile Arg Glu Ala Lys Arg Ser Ala Arg Pro Glu Leu Lys
1               5                   10

<210> SEQ ID NO 11
<211> LENGTH: 14
<212> TYPE: PRT
<213> ORGANISM: Homo sapiens

<400> SEQUENCE: 11

Trp Thr Leu Glu Arg Leu Lys Arg Lys Tyr Arg Asn Gln Lys
1               5                   10

<210> SEQ ID NO 12
<211> LENGTH: 14
<212> TYPE: PRT
<213> ORGANISM: Homo sapiens

<400> SEQUENCE: 12

Arg Lys Tyr Arg Asn Gln Lys Phe Lys Cys Gly Glu Asp Asn
1               5                   10

<210> SEQ ID NO 13
<211> LENGTH: 14
<212> TYPE: PRT
<213> ORGANISM: Homo sapiens

<400> SEQUENCE: 13

Asp Gly Tyr Ser Val Lys Met Lys Met Lys Tyr Tyr Ile Glu
1               5                   10

<210> SEQ ID NO 14
<211> LENGTH: 14
<212> TYPE: PRT
<213> ORGANISM: Homo sapiens

<400> SEQUENCE: 14

Lys Met Lys Tyr Tyr Ile Glu Tyr Met Glu Ser Thr Arg Asp
1               5                   10

<210> SEQ ID NO 15
<211> LENGTH: 14
<212> TYPE: PRT
<213> ORGANISM: Homo sapiens

<400> SEQUENCE: 15

Asp Ser Ser Tyr Gly Glu His Pro Lys Arg Arg Lys Leu Leu
1               5                   10

<210> SEQ ID NO 16
<211> LENGTH: 14
<212> TYPE: PRT
<213> ORGANISM: Homo sapiens

<400> SEQUENCE: 16

Pro Lys Arg Arg Lys Leu Leu Glu Asp Tyr Lys Val Pro Lys
1               5                   10

<210> SEQ ID NO 17
<211> LENGTH: 14
<212> TYPE: PRT
<213> ORGANISM: Homo sapiens

<400> SEQUENCE: 17

Pro Val Val Trp His Lys Thr Val Arg Gly Arg Pro Lys Leu
1               5                   10

<210> SEQ ID NO 18
<211> LENGTH: 14
<212> TYPE: PRT
<213> ORGANISM: Homo sapiens

<400> SEQUENCE: 18

Val Arg Gly Arg Pro Lys Leu Ser Arg Lys Trp Tyr Arg Ile
1               5                   10

<210> SEQ ID NO 19
<211> LENGTH: 14
<212> TYPE: PRT
<213> ORGANISM: Homo sapiens

<400> SEQUENCE: 19

Ser Arg Lys Trp Tyr Arg Ile Leu Lys Gln Glu His Pro Glu
1               5                   10

<210> SEQ ID NO 20
<211> LENGTH: 14
<212> TYPE: PRT
<213> ORGANISM: Homo sapiens

<400> SEQUENCE: 20

Ser Glu Gly Asp Gly Thr Val His Arg Arg Lys Lys Arg Arg
1               5                   10

<210> SEQ ID NO 21
<211> LENGTH: 14
<212> TYPE: PRT
<213> ORGANISM: Homo sapiens

<400> SEQUENCE: 21

His Arg Arg Lys Lys Arg Arg Thr Cys Ser Met Val Gly Asn
1               5                   10

<210> SEQ ID NO 22
<211> LENGTH: 194
<212> TYPE: PRT
<213> ORGANISM: Homo sapiens

<400> SEQUENCE: 22

Asn Ile Met Met Thr Gln Ser Pro Ser Ser Leu Ala Val Ser Ala Gly
1               5                   10                  15

Glu Lys Val Thr Met Asn Cys Lys Ser Ser Gln Ser Ile Leu Tyr Ser
            20                  25                  30

Ser Asn His Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asn Arg Phe Thr Gly Ser Gly Ser Gly Thr Asp Phe Thr Leu Thr
65                  70                  75                  80

Ile Ser Ser Val Gln Ser Glu Asp Leu Ala Val Tyr Tyr Cys His Gln
                85                  90                  95

Tyr Leu Ser Ser Tyr Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His

<210> SEQ ID NO 23
<211> LENGTH: 205
<212> TYPE: PRT
<213> ORGANISM: Homo sapiens

<400> SEQUENCE: 23

Gln Val Gln Leu Lys Gln Ser Gly Pro Gly Leu Val Gln Pro Ser Gln
1               5                   10                  15

```
Ser Leu Ser Ile Thr Cys Thr Val Ser Gly Phe Ser Leu Ser Ser Tyr
         20                  25                  30

Gly Val His Trp Val Arg Gln Ser Pro Gly Lys Gly Leu Glu Trp Leu
         35                  40                  45

Gly Val Ile Trp Arg Ser Gly Asn Thr Asp Tyr Asn Ala Val Phe Met
 50                  55                  60

Ser Arg Leu Ser Ile Thr Lys Asp Asp Ser Lys Ser Gln Val Phe Phe
 65                  70                  75                  80

Lys Met Asn Ser Leu Gln Ala Asp Asp Thr Ala Ile Tyr Tyr Cys Ala
                 85                  90                  95

Lys Asn Phe Arg Tyr Asp Val Gly Ser Trp Phe Ala Tyr Trp Gly Gln
                100                 105                 110

Gly Thr Leu Val Thr Val Ser Ala Ala Lys Thr Thr Ala Pro Ser Val
            115                 120                 125

Tyr Pro Leu Ala Pro Val Cys Gly Asp Thr Thr Gly Ser Ser Val Thr
        130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Pro
        195                 200                 205

<210> SEQ ID NO 24
<211> LENGTH: 35
<212> TYPE: DNA
<213> ORGANISM: Homo sapiens

<400> SEQUENCE: 24
ctgcagaagc ttgcggaacc agctggcgac cccgc                               35

<210> SEQ ID NO 25
<211> LENGTH: 60
<212> TYPE: DNA
<213> ORGANISM: Homo sapiens

<400> SEQUENCE: 25
ctgcagtcta gaccttatcg tcatcgtcct tgtagtctct ccctcttacc gtcttgtgcc    60

<210> SEQ ID NO 26
<211> LENGTH: 61
<212> TYPE: DNA
<213> ORGANISM: Homo sapiens

<400> SEQUENCE: 26
tgcagcccaa gcttgggcca tggactacaa ggacgatgac gataagcacc ctaaagaag    60
g                                                                   61

<210> SEQ ID NO 27
<211> LENGTH: 30
<212> TYPE: DNA
<213> ORGANISM: Homo sapiens

<400> SEQUENCE: 27
ctgcagtcta gaatctgctc aggggtgagc                                    30
```

<210> SEQ ID NO 28
<211> LENGTH: 62
<212> TYPE: DNA
<213> ORGANISM: Homo sapiens

<400> SEQUENCE: 28
ctgcagccca agcttgggcc atggactaca aggacgatga cgataagcac cctaaaagaa    60
gg    62

<210> SEQ ID NO 29
<211> LENGTH: 38
<212> TYPE: DNA
<213> ORGANISM: Homo sapiens

<400> SEQUENCE: 29
ctgcagtcta gaacctggag gagctgcgct ctttgctg    38

<210> SEQ ID NO 30
<211> LENGTH: 14
<212> TYPE: PRT
<213> ORGANISM: Homo sapiens

<400> SEQUENCE: 30

Asn Ala Lys Val Glu Glu Pro Arg Gln Pro Leu Val Tyr Leu
1               5                   10

<210> SEQ ID NO 31
<211> LENGTH: 13
<212> TYPE: PRT
<213> ORGANISM: Homo sapiens

<400> SEQUENCE: 31

Gly Thr Arg Ser Val Gly Asp His Pro Pro Met Gly His
1               5                   10

<210> SEQ ID NO 32
<211> LENGTH: 205
<212> TYPE: PRT
<213> ORGANISM: Homo sapiens

<400> SEQUENCE: 32

Gln Val Gln Met Lys Gln Ser Gly Pro Gly Leu Val Gln Pro Ser Gln
1               5                   10                  15

Ser Leu Ser Ile Thr Cys Thr Val Ser Gly Phe Ser Leu Ser Ser Tyr
            20                  25                  30

Gly Val His Trp Val Arg Gln Ser Pro Gly Lys Gly Leu Glu Trp Leu
        35                  40                  45

Gly Val Ile Trp Arg Ser Gly Asn Thr Asp Tyr Asn Ala Val Phe Met
    50                  55                  60

Ser Arg Leu Ser Ile Thr Lys Asp Asp Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Asn Phe Arg Tyr Asp Val Gly Ser Trp Phe Ala Tyr Trp Gly Gln
            100                 105                 110

Gly Thr Leu Val Thr Val Ser Ala Ala Lys Thr Thr Ala Pro Ser Val
        115                 120                 125

Tyr Pro Leu Ala Pro Val Cys Gly Asp Thr Thr Gly Ser Ser Val Thr
    130                 135                 140

```
Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
            165                 170                 175

Leu Gln Ser Asp Leu Tyr Thr Leu Ser Ser Ser Val Thr Val Thr Ser
        180                 185                 190

Ser Thr Trp Pro Ser Gln Ser Ile Thr Cys Asn Val Pro
        195                 200                 205
```

<210> SEQ ID NO 33
<211> LENGTH: 7
<212> TYPE: PRT
<213> ORGANISM: Homo sapiens

<400> SEQUENCE: 33

```
Arg Ile Arg Glu Ala Lys Arg
1               5
```

<210> SEQ ID NO 34
<211> LENGTH: 7
<212> TYPE: PRT
<213> ORGANISM: Homo sapiens

<400> SEQUENCE: 34

```
Arg Lys Tyr Arg Asn Gln Lys
1               5
```

<210> SEQ ID NO 35
<211> LENGTH: 7
<212> TYPE: PRT
<213> ORGANISM: Homo sapiens

<400> SEQUENCE: 35

```
Lys Met Lys Tyr Tyr Ile Glu
1               5
```

<210> SEQ ID NO 36
<211> LENGTH: 7
<212> TYPE: PRT
<213> ORGANISM: Homo sapiens

<400> SEQUENCE: 36

```
Pro Lys Arg Arg Lys Leu Leu
1               5
```

<210> SEQ ID NO 37
<211> LENGTH: 7
<212> TYPE: PRT
<213> ORGANISM: Homo sapiens

<400> SEQUENCE: 37

```
Arg Pro Pro Tyr Arg Trp Phe
1               5
```

<210> SEQ ID NO 38
<211> LENGTH: 7
<212> TYPE: PRT
<213> ORGANISM: Homo sapiens

<400> SEQUENCE: 38

```
Lys Arg Trp Cys Leu Phe Pro
1               5
```

```
<210> SEQ ID NO 39
<211> LENGTH: 21
<212> TYPE: PRT
<213> ORGANISM: Homo sapiens

<400> SEQUENCE: 39

Val Pro Gly Gly Trp Trp His Val Val Leu Asn Leu Asp Thr Thr Ile
1               5                   10                  15

Ala Ile Thr Gln Asn
            20

<210> SEQ ID NO 40
<211> LENGTH: 14
<212> TYPE: PRT
<213> ORGANISM: Homo sapiens

<400> SEQUENCE: 40

Val Arg Gly Arg Pro Lys Leu Ser Arg Lys Trp Tyr Arg Ile
1               5                   10

<210> SEQ ID NO 41
<211> LENGTH: 7
<212> TYPE: PRT
<213> ORGANISM: Homo sapiens

<400> SEQUENCE: 41

His Arg Arg Lys Lys Arg Arg
1               5

<210> SEQ ID NO 42
<211> LENGTH: 11
<212> TYPE: PRT
<213> ORGANISM: Homo sapiens

<400> SEQUENCE: 42

Gln Ser Ile Leu Tyr Ser Ser Asn His Lys Asn
1               5                   10

<210> SEQ ID NO 43
<211> LENGTH: 10
<212> TYPE: PRT
<213> ORGANISM: Homo sapiens

<400> SEQUENCE: 43

Trp Ala Ser Thr Arg Glu Ser Gly Val Pro
1               5                   10

<210> SEQ ID NO 44
<211> LENGTH: 6
<212> TYPE: PRT
<213> ORGANISM: Homo sapiens

<400> SEQUENCE: 44

His Gln Tyr Leu Ser Ser
1               5

<210> SEQ ID NO 45
<211> LENGTH: 8
<212> TYPE: PRT
<213> ORGANISM: Homo sapiens

<400> SEQUENCE: 45

Gly Phe Ser Leu Ser Ser Tyr Gly
1               5
```

```
<210> SEQ ID NO 46
<211> LENGTH: 7
<212> TYPE: PRT
<213> ORGANISM: Homo sapiens

<400> SEQUENCE: 46

Ile Trp Arg Ser Gly Asn Thr
1               5

<210> SEQ ID NO 47
<211> LENGTH: 14
<212> TYPE: PRT
<213> ORGANISM: Homo sapiens

<400> SEQUENCE: 47

Ala Lys Asn Phe Arg Tyr Asp Val Gly Ser Trp Phe Ala Tyr
1               5                   10
```